United States Patent
Brandt et al.

(10) Patent No.: US 11,026,741 B2
(45) Date of Patent: *Jun. 8, 2021

(54) ELECTROSURGICAL SEAL PLATES

(71) Applicant: COVIDIEN LP, Mansfield, MA (US)

(72) Inventors: Kim V. Brandt, Loveland, CO (US); Allan G. Aquino, Longmont, CO (US)

(73) Assignee: COVIDIEN LP, Mansfield, MA (US)

( * ) Notice: Subject to any disclaimer, the term of this patent is extended or adjusted under 35 U.S.C. 154(b) by 186 days.

This patent is subject to a terminal disclaimer.

(21) Appl. No.: 16/259,366

(22) Filed: Jan. 28, 2019

(65) Prior Publication Data
US 2019/0151011 A1 May 23, 2019

Related U.S. Application Data

(60) Continuation of application No. 15/689,808, filed on Aug. 29, 2017, now Pat. No. 10,188,454, which is a
(Continued)

(51) Int. Cl.
*A61B 18/14* (2006.01)
*A61B 18/00* (2006.01)
(Continued)

(52) U.S. Cl.
CPC .......... *A61B 18/1445* (2013.01); *A61B 18/00* (2013.01); *B32B 37/12* (2013.01);
(Continued)

(58) Field of Classification Search
CPC ................ A61B 18/1445; A61B 18/00; A61B 2017/00526; B32B 38/0036; B32B 38/10;
(Continued)

(56) References Cited

U.S. PATENT DOCUMENTS

| 371,664 A | 10/1887 | Brannan et al. |
| 702,472 A | 6/1902 | Pignolet |

(Continued)

FOREIGN PATENT DOCUMENTS

| EP | 0518230 A1 | 12/1992 |
| EP | 0306123 B1 | 8/1993 |

(Continued)

OTHER PUBLICATIONS

Tinkcler L.F., "Combined Diathermy and Suction Forceps", Feb. 6, 1967 (Feb. 6, 1965), British Medical Journal Feb. 6, 1976, vol. 1, nr. 5431 p. 361, ISSN: 0007-1447.
(Continued)

*Primary Examiner* — Carl J Arbes

(57) ABSTRACT

A system for the manufacture of an end effector assembly which is configured for use with an electrosurgical instrument configured for performing an electrosurgical procedure is provided. The system includes a photolithography module that is configured to etch one or more pockets on a seal surface of the seal plate. A vacuum module is configured to raise, transfer and lower a spacer from a location remote from the pocket(s) on the seal plate to the pocket on the seal plate(s). An adhesive dispensing module is configured to dispense an adhesive into the pocket on the seal plate. An optical module is configured to monitor a volume of the adhesive dispensed within the pocket and monitor placement of the spacer within the pocket.

18 Claims, 9 Drawing Sheets

Related U.S. Application Data continuation of application No. 15/049,632, filed on Feb. 22, 2016, now Pat. No. 9,750,561, which is a continuation of application No. 14/557,767, filed on Dec. 2, 2014, now Pat. No. 9,265,552, which is a continuation of application No. 13/358,657, filed on Jan. 26, 2012, now Pat. No. 8,898,888, which is a division of application No. 12/568,282, filed on Sep. 28, 2009, now Pat. No. 8,112,871.

(51) Int. Cl.
| | |
|---|---|
| *B32B 37/12* | (2006.01) |
| *B32B 38/00* | (2006.01) |
| *B32B 38/10* | (2006.01) |
| *C23F 1/02* | (2006.01) |
| *A61B 17/00* | (2006.01) |

(52) U.S. Cl.
CPC .......... *B32B 38/0036* (2013.01); *B32B 38/10* (2013.01); *C23F 1/02* (2013.01); *A61B 2017/00526* (2013.01); *B32B 2038/0076* (2013.01); *B32B 2311/12* (2013.01); *B32B 2535/00* (2013.01); *Y10T 29/49002* (2015.01); *Y10T 29/49117* (2015.01); *Y10T 29/49204* (2015.01); *Y10T 29/49208* (2015.01); *Y10T 29/5313* (2015.01)

(58) Field of Classification Search
CPC ......... B32B 2038/0076; B32B 2311/12; B32B 2535/00; B32B 37/12; C23E 1/02; Y10T 29/49117; Y10T 29/49204; Y10T 29/49208; Y10T 29/5313; C23F 1/02
See application file for complete search history.

(56) References Cited

U.S. PATENT DOCUMENTS

| | | |
|---|---|---|
| 728,883 A | 5/1903 | Downes |
| 1,586,645 A | 6/1926 | Bierman |
| 1,813,902 A | 7/1931 | Bovie |
| 1,822,330 A | 9/1931 | Ainslie |
| 1,852,542 A | 4/1932 | Sovatkin |
| 1,908,201 A | 5/1933 | Welch et al. |
| 1,918,889 A | 7/1933 | Bacon |
| 2,002,594 A | 5/1935 | Wappler et al. |
| 2,011,169 A | 8/1935 | Wappler et al. |
| 2,031,682 A | 2/1936 | Wappler et al. |
| 2,054,149 A | 9/1936 | Wappler |
| 2,113,246 A | 4/1938 | Wappler |
| 2,141,936 A | 12/1938 | Schmitt |
| 2,176,479 A | 10/1939 | Willis |
| 2,245,030 A | 6/1941 | Gottesfeld et al. |
| 2,305,156 A | 12/1942 | Grubel |
| 5,282,799 A | 2/1994 | Rydell |
| 5,313,027 A | 5/1994 | Inoue et al. |
| 5,476,479 A | 12/1995 | Green et al. |
| 5,478,351 A | 12/1995 | Meade et al. |
| 5,480,406 A | 1/1996 | Nolan et al. |
| 5,480,409 A | 1/1996 | Riza |
| 5,482,054 A | 1/1996 | Slater et al. |
| 5,484,436 A | 1/1996 | Eggers et al. |
| 5,493,899 A | 2/1996 | Beck et al. |
| 5,496,312 A | 3/1996 | Klicek |
| 5,496,317 A | 3/1996 | Goble et al. |
| 5,496,347 A | 3/1996 | Hashiguchi et al. |
| 5,499,997 A | 3/1996 | Sharpe et al. |
| 5,501,654 A | 3/1996 | Failla et al. |
| 5,509,922 A | 4/1996 | Aranyi et al. |
| 5,512,721 A | 4/1996 | Young et al. |
| 5,514,134 A | 5/1996 | Rydell et al. |
| 5,520,702 A | 5/1996 | Sauer et al. |
| 5,527,313 A | 6/1996 | Scott et al. |
| 5,528,833 A | 6/1996 | Sakuma |
| 5,529,067 A | 6/1996 | Larsen et al. |
| 5,531,744 A | 7/1996 | Nardella et al. |
| 5,536,251 A | 7/1996 | Evard et al. |
| 5,540,684 A | 7/1996 | Hassler, Jr. |
| 5,540,685 A | 7/1996 | Parins et al. |
| 5,540,706 A | 7/1996 | Aust et al. |
| 5,540,715 A | 7/1996 | Katsaros et al. |
| 5,542,945 A | 8/1996 | Fritzsch |
| 5,549,604 A | 8/1996 | Sutcu et al. |
| 5,554,172 A | 9/1996 | Horner et al. |
| 5,558,671 A | 9/1996 | Yates |
| 5,558,672 A | 9/1996 | Edwards et al. |
| 5,562,619 A | 10/1996 | Mirarchi et al. |
| 5,562,699 A | 10/1996 | Heimberger et al. |
| 5,562,720 A | 10/1996 | Stern et al. |
| 5,564,615 A | 10/1996 | Bishop et al. |
| 5,568,859 A | 10/1996 | Levy et al. |
| 5,569,241 A | 10/1996 | Edwards |
| 5,569,243 A | 10/1996 | Kortenbach et al. |
| 5,571,100 A | 11/1996 | Goble et al. |
| 5,573,424 A | 11/1996 | Poppe |
| 5,573,534 A | 11/1996 | Stone |
| 5,573,535 A | 11/1996 | Viklund |
| 5,575,799 A | 11/1996 | Bolanos et al. |
| 5,575,805 A | 11/1996 | Li |
| 5,578,052 A | 11/1996 | Koros et al. |
| 5,579,781 A | 12/1996 | Cooke |
| 5,582,611 A | 12/1996 | Tsuruta et al. |
| 5,582,617 A | 12/1996 | Klieman et al. |
| 5,585,896 A | 12/1996 | Yamazaki et al. |
| 5,590,570 A | 1/1997 | LeMaire, III et al. |
| 5,591,181 A | 1/1997 | Stone et al. |
| 5,597,107 A | 1/1997 | Knodel et al. |
| 5,599,350 A | 2/1997 | Schulze et al. |
| 5,601,224 A | 2/1997 | Bishop et al. |
| 5,601,601 A | 2/1997 | Tal et al. |
| 5,601,641 A | 2/1997 | Stephens |
| 5,603,711 A | 2/1997 | Parins et al. |
| 5,603,723 A | 2/1997 | Aranyi et al. |
| 5,607,436 A | 3/1997 | Pratt et al. |
| 5,611,798 A | 3/1997 | Eggers |
| 5,611,808 A | 3/1997 | Hossain et al. |
| 5,611,813 A | 3/1997 | Lichtman |
| 5,618,294 A | 4/1997 | Aust et al. |
| 5,618,307 A | 4/1997 | Donlon et al. |
| 5,620,415 A | 4/1997 | Lucey et al. |
| 5,620,453 A | 4/1997 | Nallakrishnan |
| 5,620,459 A | 4/1997 | Lichtman |
| 5,624,452 A | 4/1997 | Yates |
| 5,626,578 A | 5/1997 | Tihon |
| 5,626,607 A | 5/1997 | Malecki et al. |
| 5,626,609 A | 5/1997 | Zvenyatsky et al. |
| 5,630,833 A | 5/1997 | Katsaros et al. |
| 5,637,110 A | 6/1997 | Pennybacker et al. |
| 5,637,111 A | 6/1997 | Sutcu et al. |
| 5,638,003 A | 6/1997 | Hall |
| 5,638,827 A | 6/1997 | Palmer et al. |
| 5,639,403 A | 6/1997 | Ida et al. |
| 5,643,294 A | 7/1997 | Tovey et al. |
| 5,647,869 A | 7/1997 | Goble et al. |
| 5,647,871 A | 7/1997 | Levine et al. |
| 5,649,959 A | 7/1997 | Hannam et al. |
| 5,655,650 A | 8/1997 | Naitou |
| 5,658,281 A | 8/1997 | Heard |
| D384,413 S | 9/1997 | Zlock et al. |
| 5,662,667 A | 9/1997 | Knodel |
| 5,665,100 A | 9/1997 | Yoon |
| 5,667,526 A | 9/1997 | Levin |
| 5,673,841 A | 10/1997 | Schulze et al. |
| 5,674,220 A | 10/1997 | Fox et al. |
| 5,674,229 A | 10/1997 | Tovey et al. |
| 5,681,282 A | 10/1997 | Eggers et al. |
| 5,688,270 A | 11/1997 | Yates et al. |
| 5,690,652 A | 11/1997 | Wurster et al. |
| 5,690,653 A | 11/1997 | Richardson et al. |
| 5,693,051 A | 12/1997 | Schulze et al. |
| 5,693,920 A | 12/1997 | Maeda |
| 5,695,522 A | 12/1997 | LeMaire, III et al. |
| 5,700,261 A | 12/1997 | Brinkerhoff |

(56) References Cited

U.S. PATENT DOCUMENTS

| | | |
|---|---|---|
| 5,700,270 A | 12/1997 | Peyser et al. |
| 5,702,390 A | 12/1997 | Austin et al. |
| 5,707,369 A | 1/1998 | Vaitekunas et al. |
| 5,709,680 A | 1/1998 | Yates et al. |
| 5,713,895 A | 2/1998 | Lontine et al. |
| 5,716,366 A | 2/1998 | Yates |
| 5,720,742 A | 2/1998 | Zacharias |
| 5,720,744 A | 2/1998 | Eggleston et al. |
| 5,722,421 A | 3/1998 | Francese et al. |
| 5,725,536 A | 3/1998 | Oberlin et al. |
| 5,727,428 A | 3/1998 | LeMaire, III et al. |
| 5,735,848 A | 4/1998 | Yates et al. |
| 5,735,849 A | 4/1998 | Baden et al. |
| 5,743,906 A | 4/1998 | Parins et al. |
| 5,752,973 A | 5/1998 | Kieturakis |
| 5,755,717 A | 5/1998 | Yates et al. |
| 5,759,188 A | 6/1998 | Yoon |
| 5,762,255 A | 6/1998 | Chrisman et al. |
| 5,762,609 A | 6/1998 | Benaron et al. |
| 5,766,130 A | 6/1998 | Selmonosky |
| 5,766,166 A | 6/1998 | Hooven |
| 5,766,170 A | 6/1998 | Eggers |
| 5,766,196 A | 6/1998 | Griffiths |
| 5,769,849 A | 6/1998 | Eggers |
| 5,772,655 A | 6/1998 | Bauer et al. |
| 5,772,670 A | 6/1998 | Brosa |
| 5,776,128 A | 7/1998 | Eggers |
| 5,776,130 A | 7/1998 | Buysse et al. |
| 5,776,156 A | 7/1998 | Shikhman |
| 5,779,646 A | 7/1998 | Koblish et al. |
| 5,779,701 A | 7/1998 | McBrayer et al. |
| 5,779,727 A | 7/1998 | Orejola |
| 5,781,048 A | 7/1998 | Nakao et al. |
| H1745 H | 8/1998 | Paraschac |
| 5,791,231 A | 8/1998 | Cohn et al. |
| 5,792,137 A | 8/1998 | Carr et al. |
| 5,792,165 A | 8/1998 | Klieman et al. |
| 5,792,177 A | 8/1998 | Kaseda |
| 5,797,537 A | 8/1998 | Oberlin et al. |
| 5,797,927 A | 8/1998 | Yoon |
| 5,797,938 A | 8/1998 | Paraschac et al. |
| 5,797,941 A | 8/1998 | Schulze et al. |
| 5,797,958 A | 8/1998 | Yoon |
| 5,797,959 A | 8/1998 | Castro et al. |
| 5,800,448 A | 9/1998 | Banko |
| 5,800,449 A | 9/1998 | Wales |
| 5,807,393 A | 9/1998 | Williamson, IV et al. |
| 5,810,764 A | 9/1998 | Eggers et al. |
| 5,810,805 A | 9/1998 | Sutcu et al. |
| 5,810,808 A | 9/1998 | Eggers |
| 5,810,811 A | 9/1998 | Yates et al. |
| 5,810,877 A | 9/1998 | Roth et al. |
| 5,814,043 A | 9/1998 | Shapeton |
| 5,814,054 A | 9/1998 | Kortenbach et al. |
| 5,817,083 A | 10/1998 | Shemesh et al. |
| 5,817,119 A | 10/1998 | Klieman et al. |
| 5,820,630 A | 10/1998 | Lind |
| 5,824,978 A | 10/1998 | Karasik et al. |
| 5,827,271 A | 10/1998 | Buysse et al. |
| 5,827,274 A | 10/1998 | Bonnet et al. |
| 5,827,279 A | 10/1998 | Hughett et al. |
| 5,827,281 A | 10/1998 | Levin |
| 5,827,323 A | 10/1998 | Klieman et al. |
| 5,827,548 A | 10/1998 | Lavallee et al. |
| 5,830,212 A | 11/1998 | Cartmell et al. |
| 5,833,690 A | 11/1998 | Yates et al. |
| 5,833,695 A | 11/1998 | Yoon |
| 5,836,072 A | 11/1998 | Sullivan et al. |
| D402,028 S | 12/1998 | Grimm et al. |
| 5,843,080 A | 12/1998 | Fleenor et al. |
| 5,849,020 A | 12/1998 | Long et al. |
| 5,849,022 A | 12/1998 | Sakashita et al. |
| 5,851,214 A | 12/1998 | Larsen et al. |
| 5,853,412 A | 12/1998 | Mayenberger |
| 5,859,527 A | 1/1999 | Cook |
| 5,860,976 A | 1/1999 | Billings et al. |
| 5,865,361 A | 2/1999 | Milliman et al. |
| 5,876,401 A | 3/1999 | Schulze et al. |
| 5,876,410 A | 3/1999 | Petillo |
| 5,876,412 A | 3/1999 | Piraka |
| 5,882,567 A | 3/1999 | Cavallaro et al. |
| D408,018 S | 4/1999 | McNaughton |
| 5,891,141 A | 4/1999 | Rydell |
| 5,891,142 A | 4/1999 | Eggers et al. |
| 5,893,846 A | 4/1999 | Bales et al. |
| 5,893,848 A | 4/1999 | Negus et al. |
| 5,893,863 A | 4/1999 | Yoon |
| 5,893,875 A | 4/1999 | O'Connor et al. |
| 5,893,877 A | 4/1999 | Gampp, Jr. et al. |
| 5,897,563 A | 4/1999 | Yoon et al. |
| 5,902,301 A | 5/1999 | Olig |
| 5,906,630 A | 5/1999 | Anderhub et al. |
| 5,907,140 A | 5/1999 | Smith |
| 5,908,420 A | 6/1999 | Parins et al. |
| 5,908,432 A | 6/1999 | Pan |
| 5,911,719 A | 6/1999 | Eggers |
| 5,913,874 A | 6/1999 | Berns et al. |
| 5,921,916 A | 7/1999 | Aeikens et al. |
| 5,921,984 A | 7/1999 | Sutcu et al. |
| 5,925,043 A | 7/1999 | Kumar |
| 5,928,136 A | 7/1999 | Barry |
| 5,935,126 A | 8/1999 | Riza |
| 5,938,589 A | 8/1999 | Wako et al. |
| 5,941,869 A | 8/1999 | Patterson et al. |
| 5,944,718 A | 8/1999 | Austin et al. |
| 5,951,545 A | 9/1999 | Schilling et al. |
| 5,951,546 A | 9/1999 | Lorentzen |
| 5,951,549 A | 9/1999 | Richardson et al. |
| 5,954,720 A | 9/1999 | Wilson et al. |
| 5,954,731 A | 9/1999 | Yoon |
| 5,954,733 A | 9/1999 | Yoon |
| 5,957,923 A | 9/1999 | Hahnen et al. |
| 5,957,937 A | 9/1999 | Yoon |
| 5,960,544 A | 10/1999 | Beyers |
| 5,961,514 A | 10/1999 | Long et al. |
| 5,964,758 A | 10/1999 | Dresden |
| 5,967,997 A | 10/1999 | Turturro et al. |
| D416,089 S | 11/1999 | Barton et al. |
| 5,976,132 A | 11/1999 | Morris |
| 5,984,932 A | 11/1999 | Yoon |
| 5,984,938 A | 11/1999 | Yoon |
| 5,984,939 A | 11/1999 | Yoon |
| 5,989,277 A | 11/1999 | LeMaire, III et al. |
| 5,993,466 A | 11/1999 | Yoon |
| 5,993,467 A | 11/1999 | Yoon |
| 5,993,474 A | 11/1999 | Ouchi |
| 5,997,565 A | 12/1999 | Inoue |
| 6,003,517 A | 12/1999 | Sheffield et al. |
| 6,004,332 A | 12/1999 | Yoon et al. |
| 6,004,335 A | 12/1999 | Vaitekunas et al. |
| 6,010,516 A | 1/2000 | Hulka |
| 6,010,519 A | 1/2000 | Mawhirt et al. |
| 6,017,354 A | 1/2000 | Culp et al. |
| 6,017,358 A | 1/2000 | Yoon et al. |
| 6,021,693 A | 2/2000 | Feng-Sing |
| 6,024,741 A | 2/2000 | Williamson, IV et al. |
| 6,024,743 A | 2/2000 | Edwards |
| 6,024,744 A | 2/2000 | Kese et al. |
| 6,027,522 A | 2/2000 | Palmer |
| 6,030,384 A | 2/2000 | Nezhat |
| 6,033,399 A | 3/2000 | Gines |
| 6,039,733 A | 3/2000 | Buysse et al. |
| 6,041,679 A | 3/2000 | Slater et al. |
| 6,050,995 A | 4/2000 | Durgin |
| 6,050,996 A | 4/2000 | Schmaltz et al. |
| 6,053,914 A | 4/2000 | Eggers et al. |
| 6,053,933 A | 4/2000 | Balazs et al. |
| D424,694 S | 5/2000 | Tetzlaff et al. |
| D425,201 S | 5/2000 | Tetzlaff et al. |
| 6,059,782 A | 5/2000 | Novak et al. |
| 6,063,103 A | 5/2000 | Hashiguchi |
| 6,066,139 A | 5/2000 | Ryan et al. |
| 6,071,283 A | 6/2000 | Nardella et al. |
| 6,074,386 A | 6/2000 | Goble et al. |

(56) References Cited

U.S. PATENT DOCUMENTS

| | | |
|---|---|---|
| 6,077,287 A | 6/2000 | Taylor et al. |
| 6,080,180 A | 6/2000 | Yoon et al. |
| RE36,795 E | 7/2000 | Rydell |
| 6,083,150 A | 7/2000 | Aznoian et al. |
| 6,083,223 A | 7/2000 | Baker |
| 6,086,586 A | 7/2000 | Hooven |
| 6,086,601 A | 7/2000 | Yoon |
| 6,090,107 A | 7/2000 | Borgmeier et al. |
| 6,090,123 A | 7/2000 | Culp et al. |
| 6,096,037 A | 8/2000 | Mulier et al. |
| 6,099,537 A | 8/2000 | Sugai et al. |
| 6,099,550 A | 8/2000 | Yoon |
| 6,102,909 A | 8/2000 | Chen et al. |
| 6,106,542 A | 8/2000 | Toybin et al. |
| 6,110,171 A | 8/2000 | Rydell |
| 6,113,596 A | 9/2000 | Hooven et al. |
| 6,113,598 A | 9/2000 | Baker |
| 6,117,158 A | 9/2000 | Measamer et al. |
| 6,122,549 A | 9/2000 | Sharkey et al. |
| 6,123,701 A | 9/2000 | Nezhat |
| H1904 H | 10/2000 | Yates et al. |
| 6,126,658 A | 10/2000 | Baker |
| 6,126,665 A | 10/2000 | Yoon |
| 6,139,563 A | 10/2000 | Cosgrove, III et al. |
| 6,143,005 A | 11/2000 | Yoon et al. |
| 6,152,923 A | 11/2000 | Ryan |
| 6,152,924 A | 11/2000 | Parins |
| 6,159,217 A | 12/2000 | Robie et al. |
| 6,162,220 A | 12/2000 | Nezhat |
| 6,171,316 B1 | 1/2001 | Kovac et al. |
| 6,174,309 B1 | 1/2001 | Wrublewski et al. |
| 6,174,310 B1 | 1/2001 | Kirwan, Jr. |
| 6,178,628 B1 | 1/2001 | Clemens et al. |
| 6,179,834 B1 | 1/2001 | Buysse et al. |
| 6,179,837 B1 | 1/2001 | Hooven |
| 6,183,467 B1 | 2/2001 | Shapeton et al. |
| 6,187,003 B1 | 2/2001 | Buysse et al. |
| 6,190,386 B1 | 2/2001 | Rydell |
| 6,190,399 B1 | 2/2001 | Palmer et al. |
| 6,190,400 B1 | 2/2001 | Van De Moer et al. |
| 6,193,709 B1 | 2/2001 | Miyawaki et al. |
| 6,193,718 B1 | 2/2001 | Kortenbach et al. |
| 6,206,876 B1 | 3/2001 | Levine et al. |
| 6,206,877 B1 | 3/2001 | Kese et al. |
| 6,206,893 B1 | 3/2001 | Klein et al. |
| 6,214,028 B1 | 4/2001 | Yoon et al. |
| 6,217,602 B1 | 4/2001 | Redmon |
| 6,217,615 B1 | 4/2001 | Sioshansi et al. |
| 6,221,039 B1 | 4/2001 | Durgin et al. |
| 6,223,100 B1 | 4/2001 | Green |
| 6,224,593 B1 | 5/2001 | Ryan et al. |
| 6,224,614 B1 | 5/2001 | Yoon |
| 6,228,080 B1 | 5/2001 | Gines |
| 6,228,083 B1 | 5/2001 | Lands et al. |
| 6,248,124 B1 | 6/2001 | Pedros et al. |
| 6,248,944 B1 | 6/2001 | Ito |
| 6,261,307 B1 | 7/2001 | Yoon et al. |
| 6,267,758 B1 | 7/2001 | Daw et al. |
| 6,267,761 B1 | 7/2001 | Ryan |
| 6,270,497 B1 | 8/2001 | Sekino et al. |
| 6,270,508 B1 | 8/2001 | Klieman et al. |
| 6,273,887 B1 | 8/2001 | Yamauchi et al. |
| 6,277,117 B1 | 8/2001 | Tetzlaff et al. |
| 6,280,458 B1 | 8/2001 | Boche et al. |
| 6,283,961 B1 | 9/2001 | Underwood et al. |
| D449,886 S | 10/2001 | Tetzlaff et al. |
| 6,298,550 B1 | 10/2001 | Kirwan, Jr. |
| 6,302,424 B1 | 10/2001 | Gisinger et al. |
| 6,309,404 B1 | 10/2001 | Krzyzanowski |
| 6,319,262 B1 | 11/2001 | Bates et al. |
| 6,319,451 B1 | 11/2001 | Brune |
| 6,322,561 B1 | 11/2001 | Eggers et al. |
| 6,322,580 B1 | 11/2001 | Kanner |
| 6,325,795 B1 | 12/2001 | Lindemann et al. |
| 6,325,811 B1 | 12/2001 | Messerly |
| 6,329,778 B1 | 12/2001 | Culp et al. |
| 6,334,860 B1 | 1/2002 | Dorn |
| 6,334,861 B1 | 1/2002 | Chandler et al. |
| D453,923 S | 2/2002 | Olson |
| 6,345,532 B1 | 2/2002 | Coudray et al. |
| 6,350,264 B1 | 2/2002 | Hooven |
| D454,951 S | 3/2002 | Bon |
| 6,352,536 B1 | 3/2002 | Buysse et al. |
| 6,358,249 B1 | 3/2002 | Chen et al. |
| 6,358,259 B1 | 3/2002 | Swain et al. |
| 6,358,268 B1 | 3/2002 | Hunt et al. |
| 6,361,534 B1 | 3/2002 | Chen et al. |
| 6,364,876 B1 | 4/2002 | Erb et al. |
| 6,364,879 B1 | 4/2002 | Chen et al. |
| D457,958 S | 5/2002 | Dycus et al. |
| D457,959 S | 5/2002 | Tetzlaff et al. |
| 6,385,265 B1 | 5/2002 | Duffy et al. |
| 6,387,094 B1 | 5/2002 | Eitenmuller |
| 6,391,035 B1 | 5/2002 | Appleby et al. |
| 6,398,779 B1 | 6/2002 | Buysse et al. |
| 6,402,747 B1 | 6/2002 | Lindemann et al. |
| 6,409,728 B1 | 6/2002 | Ehr et al. |
| H2037 H | 7/2002 | Yates et al. |
| 6,419,675 B1 | 7/2002 | Gallo, Sr. |
| 6,425,896 B1 | 7/2002 | Baltschun et al. |
| 6,432,112 B2 | 8/2002 | Brock et al. |
| 6,440,130 B1 | 8/2002 | Mulier et al. |
| 6,440,144 B1 | 8/2002 | Bacher |
| 6,443,952 B1 | 9/2002 | Mulier et al. |
| 6,443,970 B1 | 9/2002 | Schulze et al. |
| 6,451,018 B1 | 9/2002 | Lands et al. |
| 6,458,125 B1 | 10/2002 | Cosmescu |
| 6,458,128 B1 | 10/2002 | Schulze |
| 6,458,129 B2 | 10/2002 | Scarfi |
| 6,458,130 B1 | 10/2002 | Frazier et al. |
| 6,461,352 B2 | 10/2002 | Morgan et al. |
| 6,461,368 B2 | 10/2002 | Fogarty et al. |
| 6,464,701 B1 | 10/2002 | Hooven et al. |
| 6,464,702 B2 | 10/2002 | Schulze et al. |
| 6,464,704 B2 | 10/2002 | Schmaltz et al. |
| 6,471,696 B1 | 10/2002 | Berube et al. |
| D465,281 S | 11/2002 | Lang |
| D466,209 S | 11/2002 | Bon |
| 6,485,489 B2 | 11/2002 | Teirstein et al. |
| 6,488,680 B1 | 12/2002 | Francischelli et al. |
| 6,494,888 B1 | 12/2002 | Laufer et al. |
| 6,500,176 B1 | 12/2002 | Truckai et al. |
| 6,506,196 B1 | 1/2003 | Laufer |
| 6,508,815 B1 | 1/2003 | Strul et al. |
| 6,511,480 B1 | 1/2003 | Tetzlaff et al. |
| 6,514,215 B1 | 2/2003 | Ouchi |
| 6,514,252 B2 | 2/2003 | Nezhat et al. |
| 6,517,536 B2 | 2/2003 | Hooven et al. |
| 6,517,539 B1 | 2/2003 | Smith et al. |
| 6,527,771 B1 | 3/2003 | Weadock et al. |
| 6,533,784 B2 | 3/2003 | Truckai et al. |
| 6,537,272 B2 | 3/2003 | Christopherson et al. |
| 6,540,745 B1 | 4/2003 | Fairbourn et al. |
| 6,545,239 B2 | 4/2003 | Spedale et al. |
| 6,554,844 B2 | 4/2003 | Lee et al. |
| 6,558,385 B1 | 5/2003 | McClurken et al. |
| 6,562,037 B2 | 5/2003 | Paton et al. |
| 6,569,105 B1 | 5/2003 | Kortenbach et al. |
| 6,582,450 B2 | 6/2003 | Ouchi |
| 6,585,735 B1 | 7/2003 | Frazier et al. |
| 6,602,252 B2 | 8/2003 | Mollenauer |
| 6,605,790 B2 | 8/2003 | Yoshida |
| 6,610,060 B2 | 8/2003 | Mulier et al. |
| 6,613,048 B2 | 9/2003 | Mulier et al. |
| 6,616,654 B2 | 9/2003 | Mollenauer |
| 6,616,658 B2 | 9/2003 | Ineson |
| 6,616,661 B2 | 9/2003 | Wellman et al. |
| 6,620,161 B2 | 9/2003 | Schulze et al. |
| 6,620,184 B2 | 9/2003 | de Laforcade et al. |
| 6,623,482 B2 | 9/2003 | Pendekanti et al. |
| 6,626,901 B1 | 9/2003 | Treat et al. |
| 6,629,534 B1 | 10/2003 | St. Goar et al. |
| 6,638,287 B2 | 10/2003 | Danitz et al. |
| 6,641,595 B1 | 11/2003 | Moran et al. |

(56) References Cited

U.S. PATENT DOCUMENTS

| | | |
|---|---|---|
| 6,652,514 B2 | 11/2003 | Ellman et al. |
| 6,652,518 B2 | 11/2003 | Wellman et al. |
| 6,652,521 B2 | 11/2003 | Schulze |
| 6,656,173 B1 | 12/2003 | Palermo |
| 6,656,175 B2 | 12/2003 | Francischelli et al. |
| 6,656,177 B2 | 12/2003 | Truckai et al. |
| 6,660,072 B2 | 12/2003 | Chatterjee |
| 6,663,639 B1 | 12/2003 | Laufer et al. |
| 6,663,641 B1 | 12/2003 | Kovac et al. |
| 6,666,854 B1 | 12/2003 | Lange |
| 6,669,696 B2 | 12/2003 | Bacher et al. |
| 6,673,092 B1 | 1/2004 | Bacher |
| 6,676,660 B2 | 1/2004 | Wampler et al. |
| 6,676,676 B2 | 1/2004 | Danitz et al. |
| 6,679,882 B1 | 1/2004 | Kornerup |
| 6,682,527 B2 | 1/2004 | Strul |
| 6,682,528 B2 | 1/2004 | Frazier et al. |
| 6,685,704 B2 | 2/2004 | Greep |
| 6,685,724 B1 | 2/2004 | Haluck |
| 6,689,131 B2 | 2/2004 | McClurken |
| 6,692,445 B2 | 2/2004 | Roberts et al. |
| 6,693,246 B1 | 2/2004 | Rudolph et al. |
| 6,695,840 B2 | 2/2004 | Schulze |
| 6,702,810 B2 | 3/2004 | McClurken et al. |
| 6,723,092 B2 | 4/2004 | Brown et al. |
| 6,726,068 B2 | 4/2004 | Miller |
| 6,726,686 B2 | 4/2004 | Buysse et al. |
| 6,726,694 B2 | 4/2004 | Blatter et al. |
| 6,733,498 B2 | 5/2004 | Paton et al. |
| 6,733,501 B2 | 5/2004 | Levine |
| 6,736,813 B2 | 5/2004 | Yamauchi et al. |
| 6,743,229 B2 | 6/2004 | Buysse et al. |
| 6,743,230 B2 | 6/2004 | Lutze et al. |
| 6,743,239 B1 | 6/2004 | Kuehn et al. |
| 6,743,240 B2 | 6/2004 | Smith et al. |
| 6,755,338 B2 | 6/2004 | Hahnen et al. |
| 6,755,824 B2 | 6/2004 | Jain et al. |
| 6,755,843 B2 | 6/2004 | Chung et al. |
| 6,756,553 B1 | 6/2004 | Yamaguchi et al. |
| 6,757,977 B2 | 7/2004 | Dambal et al. |
| D493,888 S | 8/2004 | Reschke |
| 6,770,072 B1 | 8/2004 | Truckai et al. |
| 6,773,409 B2 | 8/2004 | Truckai et al. |
| 6,773,432 B1 | 8/2004 | Clayman et al. |
| 6,773,434 B2 | 8/2004 | Ciarrocca |
| 6,773,435 B2 | 8/2004 | Schulze et al. |
| 6,773,441 B1 | 8/2004 | Laufer et al. |
| 6,775,575 B2 | 8/2004 | Bommannan et al. |
| 6,776,780 B2 | 8/2004 | Mulier et al. |
| 6,784,405 B2 | 8/2004 | Flugstad et al. |
| 6,786,905 B2 | 9/2004 | Swanson et al. |
| 6,790,217 B2 | 9/2004 | Schulze et al. |
| 6,796,981 B2 | 9/2004 | Wham et al. |
| D496,997 S | 10/2004 | Dycus et al. |
| 6,800,825 B1 | 10/2004 | Sasaki et al. |
| 6,802,843 B2 | 10/2004 | Truckai et al. |
| 6,808,525 B2 | 10/2004 | Latterell et al. |
| D499,181 S | 11/2004 | Dycus et al. |
| 6,818,000 B2 | 11/2004 | Muller et al. |
| 6,818,007 B1 | 11/2004 | Dampney et al. |
| 6,821,273 B2 | 11/2004 | Mollenauer |
| 6,821,285 B2 | 11/2004 | Laufer et al. |
| 6,824,547 B2 | 11/2004 | Wilson, Jr. et al. |
| 6,830,174 B2 | 12/2004 | Hillstead et al. |
| 6,835,200 B2 | 12/2004 | Laufer et al. |
| 6,843,789 B2 | 1/2005 | Goble |
| 6,857,357 B2 | 2/2005 | Fujii |
| 6,858,028 B2 | 2/2005 | Mulier et al. |
| D502,994 S | 3/2005 | Blake, III |
| 6,860,880 B2 | 3/2005 | Treat et al. |
| 6,878,147 B2 | 4/2005 | Prakash et al. |
| 6,887,240 B1 | 5/2005 | Lands et al. |
| 6,889,116 B2 | 5/2005 | Jinno |
| 6,905,497 B2 | 6/2005 | Truckai et al. |
| 6,908,463 B2 | 6/2005 | Treat et al. |
| 6,914,201 B2 | 7/2005 | Van Vooren et al. |
| 6,926,716 B2 | 8/2005 | Baker et al. |
| 6,929,644 B2 | 8/2005 | Truckai et al. |
| 6,932,810 B2 | 8/2005 | Ryan |
| 6,932,816 B2 | 8/2005 | Phan |
| 6,934,134 B2 | 8/2005 | Mori et al. |
| 6,936,061 B2 | 8/2005 | Sasaki |
| D509,297 S | 9/2005 | Wells |
| 6,942,662 B2 | 9/2005 | Goble et al. |
| 6,943,311 B2 | 9/2005 | Miyako |
| 6,951,559 B1 | 10/2005 | Greep |
| 6,953,430 B2 | 10/2005 | Kidooka |
| 6,953,461 B2 | 10/2005 | McClurken et al. |
| 6,958,070 B2 | 10/2005 | Witt et al. |
| 6,960,210 B2 | 11/2005 | Lands et al. |
| 6,964,662 B2 | 11/2005 | Kidooka |
| 6,966,907 B2 | 11/2005 | Goble |
| 6,972,017 B2 | 12/2005 | Smith et al. |
| 6,974,452 B1 | 12/2005 | Gille et al. |
| 6,976,492 B2 | 12/2005 | Ingle et al. |
| 6,977,495 B2 | 12/2005 | Donofrio |
| 6,979,786 B2 | 12/2005 | Aukland et al. |
| 6,981,628 B2 | 1/2006 | Wales |
| 6,987,244 B2 | 1/2006 | Bauer |
| 6,989,017 B2 | 1/2006 | Howell et al. |
| 6,994,707 B2 | 2/2006 | Ellman et al. |
| 6,994,709 B2 | 2/2006 | Iida |
| 6,997,931 B2 | 2/2006 | Sauer et al. |
| 7,001,381 B2 | 2/2006 | Harano et al. |
| 7,001,408 B2 | 2/2006 | Knodel et al. |
| 7,011,657 B2 | 3/2006 | Truckai et al. |
| 7,025,763 B2 | 4/2006 | Karasawa et al. |
| 7,033,354 B2 | 4/2006 | Keppel |
| 7,033,356 B2 | 4/2006 | Latterell et al. |
| 7,041,102 B2 | 5/2006 | Truckai et al. |
| 7,044,948 B2 | 5/2006 | Keppel |
| 7,052,489 B2 | 5/2006 | Griego et al. |
| 7,052,496 B2 | 5/2006 | Yamauchi |
| 7,063,699 B2 | 6/2006 | Hess et al. |
| 7,063,715 B2 | 6/2006 | Onuki et al. |
| D525,361 S | 7/2006 | Hushka |
| 7,070,597 B2 | 7/2006 | Truckai et al. |
| 7,083,618 B2 | 8/2006 | Couture et al. |
| 7,083,619 B2 | 8/2006 | Truckai et al. |
| 7,083,620 B2 | 8/2006 | Jahns et al. |
| 7,087,051 B2 | 8/2006 | Bourne et al. |
| 7,087,054 B2 | 8/2006 | Truckai et al. |
| 7,090,673 B2 | 8/2006 | Dycus et al. |
| 7,090,689 B2 | 8/2006 | Nagase et al. |
| 7,101,371 B2 | 9/2006 | Dycus et al. |
| 7,101,372 B2 | 9/2006 | Dycus et al. |
| 7,101,373 B2 | 9/2006 | Dycus et al. |
| 7,103,947 B2 | 9/2006 | Sartor et al. |
| 7,107,124 B2 | 9/2006 | Green |
| 7,108,694 B2 | 9/2006 | Miura et al. |
| 7,112,199 B2 | 9/2006 | Cosmescu |
| 7,112,201 B2 | 9/2006 | Truckai et al. |
| D531,311 S | 10/2006 | Guerra et al. |
| 7,115,123 B2 | 10/2006 | Knowlton et al. |
| 7,115,139 B2 | 10/2006 | McClurken et al. |
| 7,118,570 B2 | 10/2006 | Tetzlaff et al. |
| 7,118,587 B2 | 10/2006 | Dycus et al. |
| 7,131,860 B2 | 11/2006 | Sartor et al. |
| 7,131,970 B2 | 11/2006 | Moses et al. |
| 7,131,971 B2 | 11/2006 | Dycus et al. |
| 7,135,018 B2 | 11/2006 | Ryan et al. |
| 7,135,020 B2 | 11/2006 | Lawes et al. |
| 7,137,980 B2 | 11/2006 | Buysse et al. |
| D533,274 S | 12/2006 | Visconti et al. |
| D533,942 S | 12/2006 | Kerr et al. |
| 7,145,757 B2 | 12/2006 | Shea et al. |
| 7,147,632 B2 | 12/2006 | Prakash et al. |
| 7,147,638 B2 | 12/2006 | Chapman et al. |
| 7,150,097 B2 | 12/2006 | Sremcich et al. |
| 7,150,749 B2 | 12/2006 | Dycus et al. |
| 7,153,314 B2 | 12/2006 | Laufer et al. |
| D535,027 S | 1/2007 | James et al. |
| 7,156,842 B2 | 1/2007 | Sartor et al. |
| 7,156,846 B2 | 1/2007 | Dycus et al. |

(56) References Cited

U.S. PATENT DOCUMENTS

| | | |
|---|---|---|
| 7,160,298 B2 | 1/2007 | Lawes et al. |
| 7,160,299 B2 | 1/2007 | Baily |
| 7,166,106 B2 | 1/2007 | Bartel et al. |
| 7,169,145 B2 | 1/2007 | Isaacson et al. |
| 7,169,146 B2 | 1/2007 | Truckai et al. |
| 7,179,255 B2 | 2/2007 | Lettice et al. |
| 7,179,258 B2 | 2/2007 | Buysse et al. |
| 7,184,820 B2 | 2/2007 | Jersey-Willuhn et al. |
| D538,932 S | 3/2007 | Malik |
| 7,189,233 B2 | 3/2007 | Truckai et al. |
| 7,195,631 B2 | 3/2007 | Dumbauld |
| D541,418 S | 4/2007 | Schechter et al. |
| 7,204,835 B2 | 4/2007 | Latterell et al. |
| 7,207,990 B2 | 4/2007 | Lands et al. |
| 7,208,005 B2 | 4/2007 | Frecker et al. |
| D541,611 S | 5/2007 | Aglassinger |
| D541,938 S | 5/2007 | Kerr et al. |
| 7,211,084 B2 | 5/2007 | Goble et al. |
| 7,223,264 B2 | 5/2007 | Daniel et al. |
| 7,223,265 B2 | 5/2007 | Keppel |
| D545,432 S | 6/2007 | Watanabe |
| 7,232,440 B2 | 6/2007 | Dumbauld et al. |
| D547,154 S | 7/2007 | Lee |
| 7,238,184 B2 | 7/2007 | Megerman et al. |
| 7,241,288 B2 | 7/2007 | Braun |
| 7,241,296 B2 | 7/2007 | Buysse et al. |
| 7,244,257 B2 | 7/2007 | Podhajsky et al. |
| 7,246,734 B2 | 7/2007 | Shelton, IV |
| 7,248,944 B2 | 7/2007 | Green |
| 7,252,667 B2 | 8/2007 | Moses et al. |
| 7,254,433 B2 | 8/2007 | Diab et al. |
| 7,255,697 B2 | 8/2007 | Dycus et al. |
| 7,267,677 B2 | 9/2007 | Johnson et al. |
| 7,270,660 B2 | 9/2007 | Ryan |
| 7,270,664 B2 | 9/2007 | Johnson et al. |
| 7,276,068 B2 | 10/2007 | Johnson et al. |
| 7,288,103 B2 | 10/2007 | Suzuki |
| 7,291,161 B2 | 11/2007 | Hooven |
| 7,300,435 B2 | 11/2007 | Wham et al. |
| 7,303,557 B2 | 12/2007 | Wham et al. |
| 7,311,709 B2 | 12/2007 | Truckai et al. |
| 7,314,471 B2 | 1/2008 | Holman |
| 7,318,823 B2 | 1/2008 | Sharps et al. |
| 7,326,202 B2 | 2/2008 | McGaffigan |
| 7,329,256 B2 | 2/2008 | Johnson et al. |
| 7,329,257 B2 | 2/2008 | Kanehira et al. |
| D564,662 S | 3/2008 | Moses et al. |
| 7,338,526 B2 | 3/2008 | Steinberg |
| 7,342,754 B2 | 3/2008 | Fitzgerald et al. |
| 7,344,268 B2 | 3/2008 | Jigamian |
| 7,347,864 B2 | 3/2008 | Vargas |
| D567,943 S | 4/2008 | Moses et al. |
| 7,354,440 B2 | 4/2008 | Truckal et al. |
| 7,367,976 B2 | 5/2008 | Lawes et al. |
| 7,377,920 B2 | 5/2008 | Buysse et al. |
| 7,384,420 B2 | 6/2008 | Dycus et al. |
| 7,384,421 B2 | 6/2008 | Hushka |
| 7,396,265 B2 | 7/2008 | Darley et al. |
| 7,396,336 B2 | 7/2008 | Orszulak et al. |
| 7,396,356 B2 | 7/2008 | Mollenauer |
| D575,395 S | 8/2008 | Hushka |
| D575,401 S | 8/2008 | Hixson et al. |
| 7,422,592 B2 | 9/2008 | Morley et al. |
| 7,425,835 B2 | 9/2008 | Eisele |
| 7,431,721 B2 | 10/2008 | Paton et al. |
| 7,435,249 B2 | 10/2008 | Buysse et al. |
| 7,438,714 B2 | 10/2008 | Phan |
| 7,442,193 B2 | 10/2008 | Shields et al. |
| 7,442,194 B2 | 10/2008 | Dumbauld et al. |
| 7,445,621 B2 | 11/2008 | Dumbauld et al. |
| D582,038 S | 12/2008 | Swoyer et al. |
| 7,458,972 B2 | 12/2008 | Keppel |
| 7,473,253 B2 | 1/2009 | Dycus et al. |
| 7,481,810 B2 | 1/2009 | Dumbauld et al. |
| 7,487,780 B2 | 2/2009 | Hooven |
| 7,491,201 B2 | 2/2009 | Shields et al. |
| 7,491,202 B2 | 2/2009 | Odom et al. |
| 7,500,975 B2 | 3/2009 | Cunningham et al. |
| 7,503,474 B2 | 3/2009 | Hillstead et al. |
| 7,510,556 B2 | 3/2009 | Nguyen et al. |
| 7,513,898 B2 | 4/2009 | Johnson et al. |
| 7,517,351 B2 | 4/2009 | Culp et al. |
| 7,540,872 B2 | 6/2009 | Schechter et al. |
| 7,549,995 B2 | 6/2009 | Schultz |
| 7,553,312 B2 | 6/2009 | Tetzlaff et al. |
| 7,553,686 B2 | 6/2009 | George et al. |
| 7,569,626 B2 | 8/2009 | Truckai |
| 7,582,087 B2 | 9/2009 | Tetzlaff et al. |
| 7,588,565 B2 | 9/2009 | Marchitto et al. |
| 7,594,313 B2 | 9/2009 | Prakash et al. |
| 7,594,916 B2 | 9/2009 | Weinberg |
| 7,597,693 B2 | 10/2009 | Garrison |
| 7,621,910 B2 | 11/2009 | Sugi |
| 7,624,186 B2 | 11/2009 | Tanida |
| 7,625,370 B2 | 12/2009 | Hart et al. |
| 7,628,791 B2 | 12/2009 | Garrison et al. |
| 7,628,792 B2 | 12/2009 | Guerra |
| 7,637,409 B2 | 12/2009 | Marczyk |
| 7,641,653 B2 | 1/2010 | Dalla Betta et al. |
| 7,651,493 B2 | 1/2010 | Arts et al. |
| 7,651,494 B2 | 1/2010 | McClurken et al. |
| 7,655,004 B2 | 2/2010 | Long |
| 7,655,007 B2 | 2/2010 | Baily |
| 7,668,597 B2 | 2/2010 | Engmark et al. |
| 7,678,111 B2 | 3/2010 | Mulier et al. |
| 7,686,804 B2 | 3/2010 | Johnson et al. |
| 7,686,827 B2 | 3/2010 | Hushka |
| 7,708,735 B2 | 5/2010 | Chapman et al. |
| 7,717,115 B2 | 5/2010 | Barrett et al. |
| 7,717,904 B2 | 5/2010 | Suzuki et al. |
| 7,717,914 B2 | 5/2010 | Kimura |
| 7,717,915 B2 | 5/2010 | Miyazawa |
| 7,722,607 B2 | 5/2010 | Dumbauld et al. |
| D617,900 S | 6/2010 | Kingsley et al. |
| D617,901 S | 6/2010 | Unger et al. |
| D617,902 S | 6/2010 | Twomey et al. |
| D617,903 S | 6/2010 | Unger et al. |
| D618,798 S | 6/2010 | Olson et al. |
| 7,727,231 B2 | 6/2010 | Swanson |
| 7,731,717 B2 | 6/2010 | Odom et al. |
| 7,736,374 B2 | 6/2010 | Vaughan et al. |
| 7,744,615 B2 | 6/2010 | Couture |
| 7,749,217 B2 | 7/2010 | Podhajsky |
| 7,753,908 B2 | 7/2010 | Swanson |
| 7,753,909 B2 | 7/2010 | Chapman et al. |
| D621,503 S | 8/2010 | Otten et al. |
| 7,766,910 B2 | 8/2010 | Hixson et al. |
| 7,771,425 B2 | 8/2010 | Dycus et al. |
| 7,776,036 B2 | 8/2010 | Schechter et al. |
| 7,776,037 B2 | 8/2010 | Odom |
| 7,780,662 B2 | 8/2010 | Bahney |
| 7,780,663 B2 | 8/2010 | Yates et al. |
| 7,789,878 B2 | 9/2010 | Dumbauld et al. |
| 7,799,026 B2 | 9/2010 | Schechter et al. |
| 7,799,028 B2 | 9/2010 | Schechter et al. |
| 7,811,283 B2 | 10/2010 | Moses et al. |
| 7,819,872 B2 | 10/2010 | Johnson et al. |
| D627,462 S | 11/2010 | Kingsley |
| D628,289 S | 11/2010 | Romero |
| D628,290 S | 11/2010 | Romero |
| 7,828,798 B2 | 11/2010 | Buysse et al. |
| 7,832,408 B2 | 11/2010 | Shelton, IV et al. |
| 7,837,685 B2 | 11/2010 | Weinberg et al. |
| 7,839,674 B2 | 11/2010 | Lowrey et al. |
| 7,842,033 B2 | 11/2010 | Isaacson et al. |
| 7,846,158 B2 | 12/2010 | Podhajsky |
| 7,846,161 B2 | 12/2010 | Dumbauld et al. |
| 7,857,812 B2 | 12/2010 | Dycus et al. |
| D630,324 S | 1/2011 | Reschke |
| 7,877,852 B2 | 2/2011 | Unger et al. |
| 7,877,853 B2 | 2/2011 | Unger et al. |
| 7,879,035 B2 | 2/2011 | Garrison et al. |
| 7,887,535 B2 | 2/2011 | Lands et al. |
| 7,887,536 B2 | 2/2011 | Johnson et al. |

(56) References Cited

U.S. PATENT DOCUMENTS

| | | |
|---|---|---|
| 7,896,878 B2 | 3/2011 | Johnson et al. |
| 7,898,288 B2 | 3/2011 | Wong |
| 7,900,805 B2 | 3/2011 | Shelton, IV et al. |
| 7,901,400 B2 | 3/2011 | Wham et al. |
| 7,905,380 B2 | 3/2011 | Shelton, IV et al. |
| 7,905,881 B2 | 3/2011 | Masuda et al. |
| 7,909,820 B2 | 3/2011 | Lipson et al. |
| 7,909,823 B2 | 3/2011 | Moses et al. |
| 7,909,824 B2 | 3/2011 | Masuda et al. |
| 7,918,848 B2 | 4/2011 | Lau et al. |
| 7,922,718 B2 | 4/2011 | Moses et al. |
| 7,922,742 B2 | 4/2011 | Hillstead et al. |
| 7,922,953 B2 | 4/2011 | Guerra |
| 7,931,649 B2 | 4/2011 | Couture et al. |
| 7,935,052 B2 | 5/2011 | Dumbauld |
| 7,945,332 B2 | 5/2011 | Schechter |
| 7,947,041 B2 | 5/2011 | Tetzlaff et al. |
| 7,949,407 B2 | 5/2011 | Kaplan et al. |
| 7,951,149 B2 | 5/2011 | Carlton |
| 7,951,150 B2 | 5/2011 | Johnson et al. |
| 7,955,326 B2 | 6/2011 | Paul et al. |
| 7,955,327 B2 | 6/2011 | Sartor et al. |
| 7,955,331 B2 | 6/2011 | Truckai et al. |
| 7,955,332 B2 | 6/2011 | Arts et al. |
| 7,963,965 B2 | 6/2011 | Buysse et al. |
| 7,967,839 B2 | 6/2011 | Flock et al. |
| 7,972,328 B2 | 7/2011 | Wham et al. |
| 7,972,331 B2 | 7/2011 | Hafner |
| 7,976,544 B2 | 7/2011 | McClurken et al. |
| 7,981,113 B2 | 7/2011 | Truckai et al. |
| 7,988,507 B2 | 8/2011 | Darley et al. |
| 7,998,095 B2 | 8/2011 | McAuley |
| 8,012,150 B2 | 9/2011 | Wham et al. |
| 8,016,827 B2 | 9/2011 | Chojin |
| 8,034,049 B2 | 10/2011 | Odom et al. |
| D649,249 S | 11/2011 | Guerra |
| D649,643 S | 11/2011 | Allen, IV et al. |
| 8,048,074 B2 | 11/2011 | Masuda |
| 8,070,746 B2 | 12/2011 | Orton et al. |
| 8,070,748 B2 | 12/2011 | Hixson et al. |
| 8,075,580 B2 | 12/2011 | Makower |
| 8,089,417 B2 | 1/2012 | Popovic et al. |
| 8,092,451 B2 | 1/2012 | Schechter et al. |
| 8,104,956 B2 | 1/2012 | Blaha |
| 8,112,871 B2 | 2/2012 | Brandt et al. |
| 8,114,122 B2 | 2/2012 | Nau, Jr. |
| 8,123,743 B2 | 2/2012 | Arts et al. |
| 8,128,624 B2 | 3/2012 | Couture et al. |
| 8,128,625 B2 | 3/2012 | Odom |
| 8,133,224 B2 | 3/2012 | Geiselhart |
| 8,133,254 B2 | 3/2012 | Dumbauld et al. |
| 8,147,489 B2 | 4/2012 | Moses et al. |
| 8,469,716 B2 | 6/2013 | Fedotov et al. |
| 8,568,408 B2 | 10/2013 | Townsend et al. |
| 8,591,510 B2 | 11/2013 | Allen, IV et al. |
| 8,628,557 B2 | 1/2014 | Collings et al. |
| 8,679,098 B2 | 3/2014 | Hart |
| 8,685,009 B2 | 4/2014 | Chernov et al. |
| 8,685,021 B2 | 4/2014 | Chernov et al. |
| 8,685,056 B2 | 4/2014 | Evans et al. |
| 8,702,737 B2 | 4/2014 | Chojin et al. |
| 8,702,749 B2 | 4/2014 | Twomey |
| 8,745,840 B2 | 6/2014 | Hempstead et al. |
| 8,747,434 B2 | 6/2014 | Larson et al. |
| 8,756,785 B2 | 6/2014 | Allen, IV et al. |
| 8,784,418 B2 | 7/2014 | Romero |
| 8,840,639 B2 | 9/2014 | Gerhardt, Jr. et al. |
| 8,845,636 B2 | 9/2014 | Allen, IV et al. |
| 8,852,185 B2 | 10/2014 | Twomey |
| 8,852,228 B2 | 10/2014 | Nau, Jr. |
| 8,864,753 B2 | 10/2014 | Nau, Jr. et al. |
| 8,864,795 B2 | 10/2014 | Kerr et al. |
| 8,887,373 B2 | 11/2014 | Brandt et al. |
| 8,888,771 B2 | 11/2014 | Twomey |
| 8,898,888 B2 | 12/2014 | Brandt et al. |
| 8,900,232 B2 | 12/2014 | Ourada |
| 8,920,421 B2 | 12/2014 | Rupp |
| 8,932,293 B2 | 1/2015 | Chernov et al. |
| 8,936,614 B2 | 1/2015 | Allen, IV |
| 8,939,972 B2 | 1/2015 | Twomey |
| 8,945,175 B2 | 2/2015 | Twomey |
| 8,961,513 B2 | 2/2015 | Allen, IV et al. |
| 8,961,515 B2 | 2/2015 | Twomey et al. |
| 8,968,283 B2 | 3/2015 | Kharin |
| 8,968,305 B2 | 3/2015 | Dumbauld et al. |
| 8,968,306 B2 | 3/2015 | Unger |
| 8,968,307 B2 | 3/2015 | Evans et al. |
| 8,968,308 B2 | 3/2015 | Horner et al. |
| 8,968,309 B2 | 3/2015 | Roy et al. |
| 8,968,310 B2 | 3/2015 | Twomey et al. |
| 8,968,316 B2 | 3/2015 | Roy et al. |
| 8,968,317 B2 | 3/2015 | Evans et al. |
| 8,968,360 B2 | 3/2015 | Garrison et al. |
| 9,011,435 B2 | 4/2015 | Brandt et al. |
| 9,023,035 B2 | 5/2015 | Allen, IV et al. |
| 9,028,484 B2 | 5/2015 | Craig |
| 9,028,492 B2 | 5/2015 | Kerr et al. |
| 9,039,704 B2 | 5/2015 | Joseph |
| 9,039,732 B2 | 5/2015 | Sims et al. |
| 9,060,780 B2 | 6/2015 | Twomey et al. |
| 9,113,882 B2 | 8/2015 | Twomey et al. |
| 9,113,899 B2 | 8/2015 | Garrison et al. |
| 9,113,909 B2 | 8/2015 | Twomey et al. |
| 9,113,933 B2 | 8/2015 | Chernova et al. |
| 9,113,934 B2 | 8/2015 | Chernov et al. |
| 9,113,938 B2 | 8/2015 | Kerr |
| 9,113,940 B2 | 8/2015 | Twomey |
| 9,161,807 B2 | 10/2015 | Garrison |
| 9,259,268 B2 | 2/2016 | Behnke, II et al. |
| 9,265,552 B2 | 2/2016 | Brandt et al. |
| 9,265,565 B2 | 2/2016 | Kerr |
| 9,265,568 B2 | 2/2016 | Chernov et al. |
| 9,314,295 B2 | 4/2016 | Garrison |
| 9,333,002 B2 | 5/2016 | Garrison |
| 9,381,059 B2 | 7/2016 | Garrison |
| 9,456,870 B2 | 10/2016 | Chernov et al. |
| 9,486,220 B2 | 11/2016 | Twomey et al. |
| 9,492,221 B2 | 11/2016 | Garrison |
| 9,615,877 B2 | 4/2017 | Tyrrell et al. |
| 9,636,169 B2 | 5/2017 | Allen, IV et al. |
| 9,668,806 B2 | 6/2017 | Unger et al. |
| 9,693,816 B2 | 7/2017 | Orszulak |
| 9,750,561 B2 | 9/2017 | Brandt et al. |
| 10,188,454 B2 * | 1/2019 | Brandt .................. C23F 1/02 |
| 2002/0107517 A1 | 8/2002 | Witt et al. |
| 2002/0111624 A1 | 8/2002 | Witt et al. |
| 2002/0165469 A1 | 11/2002 | Murakami |
| 2003/0014052 A1 | 1/2003 | Buysse et al. |
| 2003/0014053 A1 | 1/2003 | Nguyen et al. |
| 2003/0018332 A1 | 1/2003 | Schmaltz et al. |
| 2003/0069570 A1 | 4/2003 | Witzel et al. |
| 2003/0109875 A1 | 6/2003 | Tetzlaff et al. |
| 2003/0114851 A1 | 6/2003 | Truckai et al. |
| 2003/0130653 A1 | 7/2003 | Sixto et al. |
| 2003/0139741 A1 | 7/2003 | Goble et al. |
| 2003/0158548 A1 | 8/2003 | Phan et al. |
| 2003/0171747 A1 | 9/2003 | Kanehira et al. |
| 2003/0181910 A1 | 9/2003 | Dycus et al. |
| 2003/0191396 A1 | 10/2003 | Sanghvi et al. |
| 2003/0216732 A1 | 11/2003 | Truckai et al. |
| 2003/0229344 A1 | 12/2003 | Dycus et al. |
| 2003/0236325 A1 | 12/2003 | Bonora |
| 2004/0064151 A1 | 4/2004 | Mollenauer |
| 2004/0073238 A1 | 4/2004 | Makower |
| 2004/0073256 A1 | 4/2004 | Marchitto et al. |
| 2004/0115296 A1 | 6/2004 | Duffin |
| 2004/0176762 A1 | 9/2004 | Lawes et al. |
| 2004/0176779 A1 | 9/2004 | Casutt et al. |
| 2004/0199181 A1 | 10/2004 | Knodel et al. |
| 2004/0224590 A1 | 11/2004 | Rawa et al. |
| 2004/0236326 A1 | 11/2004 | Schulze et al. |
| 2004/0249371 A1 | 12/2004 | Dycus et al. |
| 2004/0249374 A1 | 12/2004 | Tetzlaff et al. |
| 2004/0260281 A1 | 12/2004 | Baxter et al. |

(56) References Cited

U.S. PATENT DOCUMENTS

| | | |
|---|---|---|
| 2005/0004564 A1 | 1/2005 | Wham et al. |
| 2005/0004569 A1 | 1/2005 | Witt et al. |
| 2005/0021025 A1 | 1/2005 | Buysse et al. |
| 2005/0059858 A1 | 3/2005 | Frith et al. |
| 2005/0059934 A1 | 3/2005 | Wenchell et al. |
| 2005/0090817 A1 | 4/2005 | Phan |
| 2005/0096645 A1 | 5/2005 | Wellman et al. |
| 2005/0149017 A1 | 7/2005 | Dycus |
| 2005/0254081 A1 | 11/2005 | Ryu et al. |
| 2005/0283148 A1 | 12/2005 | Janssen et al. |
| 2006/0052779 A1 | 3/2006 | Hammill |
| 2006/0064086 A1 | 3/2006 | Odom |
| 2006/0079933 A1 | 4/2006 | Hushka et al. |
| 2006/0084973 A1 | 4/2006 | Hushka |
| 2006/0111711 A1 | 5/2006 | Goble |
| 2006/0173452 A1 | 8/2006 | Buysse et al. |
| 2006/0190035 A1 | 8/2006 | Hushka et al. |
| 2006/0217709 A1 | 9/2006 | Couture et al. |
| 2006/0224053 A1 | 10/2006 | Black et al. |
| 2006/0253126 A1 | 11/2006 | Bjerken et al. |
| 2006/0259036 A1 | 11/2006 | Tetzlaff et al. |
| 2006/0264922 A1 | 11/2006 | Sartor et al. |
| 2006/0271030 A1 | 11/2006 | Francis et al. |
| 2006/0271038 A1 | 11/2006 | Johnson et al. |
| 2006/0287641 A1 | 12/2006 | Perlin |
| 2007/0027447 A1 | 2/2007 | Theroux et al. |
| 2007/0043337 A1 | 2/2007 | McAuley |
| 2007/0043353 A1 | 2/2007 | Dycus et al. |
| 2007/0062017 A1 | 3/2007 | Dycus et al. |
| 2007/0118115 A1 | 5/2007 | Artale et al. |
| 2007/0173811 A1 | 7/2007 | Couture et al. |
| 2007/0173813 A1 | 7/2007 | Odom |
| 2007/0198011 A1 | 8/2007 | Sugita |
| 2007/0225695 A1 | 9/2007 | Mayer et al. |
| 2007/0255279 A1 | 11/2007 | Buysse et al. |
| 2007/0260238 A1 | 11/2007 | Guerra |
| 2007/0260242 A1 | 11/2007 | Dycus et al. |
| 2007/0265616 A1 | 11/2007 | Couture et al. |
| 2007/0265620 A1 | 11/2007 | Kraas et al. |
| 2008/0004616 A1 | 1/2008 | Patrick |
| 2008/0015575 A1 | 1/2008 | Odom et al. |
| 2008/0033428 A1 | 2/2008 | Artale et al. |
| 2008/0039831 A1 | 2/2008 | Odom et al. |
| 2008/0039835 A1 | 2/2008 | Johnson et al. |
| 2008/0045947 A1 | 2/2008 | Johnson et al. |
| 2008/0046122 A1 | 2/2008 | Manzo et al. |
| 2008/0058802 A1 | 3/2008 | Couture et al. |
| 2008/0082100 A1 | 4/2008 | Orton et al. |
| 2008/0125767 A1 | 5/2008 | Blaha |
| 2008/0125797 A1 | 5/2008 | Kelleher |
| 2008/0171938 A1 | 7/2008 | Masuda et al. |
| 2008/0172051 A1 | 7/2008 | Masuda et al. |
| 2008/0195093 A1 | 8/2008 | Couture et al. |
| 2008/0208289 A1 | 8/2008 | Darley et al. |
| 2008/0215050 A1 | 9/2008 | Bakos |
| 2008/0234701 A1 | 9/2008 | Morales et al. |
| 2008/0243106 A1 | 10/2008 | Coe et al. |
| 2008/0243120 A1 | 10/2008 | Lawes et al. |
| 2008/0243158 A1 | 10/2008 | Morgan |
| 2008/0249523 A1 | 10/2008 | McPherson et al. |
| 2008/0249527 A1 | 10/2008 | Couture |
| 2008/0271360 A1 | 11/2008 | Barfield |
| 2008/0281311 A1 | 11/2008 | Dunning et al. |
| 2008/0300580 A1 | 12/2008 | Shelton, IV et al. |
| 2008/0312653 A1 | 12/2008 | Arts et al. |
| 2008/0319292 A1 | 12/2008 | Say et al. |
| 2008/0319442 A1 | 12/2008 | Unger et al. |
| 2009/0012556 A1 | 1/2009 | Boudreaux et al. |
| 2009/0015832 A1 | 1/2009 | Popovic et al. |
| 2009/0024126 A1 | 1/2009 | Artale et al. |
| 2009/0036881 A1 | 2/2009 | Artale et al. |
| 2009/0036899 A1 | 2/2009 | Carlton et al. |
| 2009/0043304 A1 | 2/2009 | Tetzlaff et al. |
| 2009/0048596 A1 | 2/2009 | Shields et al. |
| 2009/0054894 A1 | 2/2009 | Yachi |
| 2009/0062794 A1 | 3/2009 | Buysse et al. |
| 2009/0065565 A1 | 3/2009 | Cao |
| 2009/0076506 A1 | 3/2009 | Baker |
| 2009/0076534 A1 | 3/2009 | Shelton, IV et al. |
| 2009/0082766 A1 | 3/2009 | Unger et al. |
| 2009/0082767 A1 | 3/2009 | Unger et al. |
| 2009/0082769 A1 | 3/2009 | Unger et al. |
| 2009/0088738 A1 | 4/2009 | Guerra et al. |
| 2009/0088739 A1 | 4/2009 | Hushka et al. |
| 2009/0088740 A1 | 4/2009 | Guerra et al. |
| 2009/0088741 A1 | 4/2009 | Hushka et al. |
| 2009/0088744 A1 | 4/2009 | Townsend |
| 2009/0088745 A1 | 4/2009 | Hushka et al. |
| 2009/0088746 A1 | 4/2009 | Hushka et al. |
| 2009/0088747 A1 | 4/2009 | Hushka et al. |
| 2009/0088748 A1 | 4/2009 | Guerra et al. |
| 2009/0088749 A1 | 4/2009 | Hushka et al. |
| 2009/0088750 A1 | 4/2009 | Hushka et al. |
| 2009/0105750 A1 | 4/2009 | Price et al. |
| 2009/0112200 A1 | 4/2009 | Eggers |
| 2009/0112206 A1 | 4/2009 | Dumbauld et al. |
| 2009/0112229 A1 | 4/2009 | Omori et al. |
| 2009/0131934 A1 | 5/2009 | Odom et al. |
| 2009/0138006 A1 | 5/2009 | Bales et al. |
| 2009/0149853 A1 | 6/2009 | Shields et al. |
| 2009/0149854 A1 | 6/2009 | Cunningham et al. |
| 2009/0157071 A1 | 6/2009 | Wham et al. |
| 2009/0157072 A1 | 6/2009 | Wham et al. |
| 2009/0157075 A1 | 6/2009 | Wham et al. |
| 2009/0171350 A1 | 7/2009 | Dycus et al. |
| 2009/0171354 A1 | 7/2009 | Deville et al. |
| 2009/0177094 A1 | 7/2009 | Brown et al. |
| 2009/0182327 A1 | 7/2009 | Unger |
| 2009/0182329 A1 | 7/2009 | Dycus |
| 2009/0187188 A1 | 7/2009 | Guerra et al. |
| 2009/0198233 A1 | 8/2009 | Chojin |
| 2009/0204114 A1 | 8/2009 | Odom |
| 2009/0204137 A1 | 8/2009 | Maxwell |
| 2009/0206126 A1 | 8/2009 | Huitema et al. |
| 2009/0209957 A1 | 8/2009 | Schmaltz et al. |
| 2009/0209960 A1 | 8/2009 | Chojin |
| 2009/0234354 A1 | 9/2009 | Johnson et al. |
| 2009/0248007 A1 | 10/2009 | Falkenstein et al. |
| 2009/0248013 A1 | 10/2009 | Falkenstein et al. |
| 2009/0248019 A1 | 10/2009 | Falkenstein et al. |
| 2009/0248020 A1 | 10/2009 | Falkenstein et al. |
| 2009/0248021 A1 | 10/2009 | McKenna |
| 2009/0248022 A1 | 10/2009 | Falkenstein et al. |
| 2009/0248050 A1 | 10/2009 | Hirai |
| 2009/0248051 A1 | 10/2009 | Masuda |
| 2009/0254080 A1 | 10/2009 | Honda |
| 2009/0254081 A1 | 10/2009 | Allison et al. |
| 2009/0261804 A1 | 10/2009 | McKenna et al. |
| 2009/0270771 A1 | 10/2009 | Takahashi |
| 2009/0292282 A9 | 11/2009 | Dycus |
| 2009/0318912 A1 | 12/2009 | Mayer et al. |
| 2010/0016857 A1 | 1/2010 | McKenna et al. |
| 2010/0023009 A1 | 1/2010 | Moses et al. |
| 2010/0030028 A1 | 2/2010 | Cabrera et al. |
| 2010/0036375 A1 | 2/2010 | Regadas |
| 2010/0042140 A1 | 2/2010 | Cunningham |
| 2010/0042142 A1 | 2/2010 | Cunningham |
| 2010/0042143 A1 | 2/2010 | Cunningham |
| 2010/0049187 A1 | 2/2010 | Carlton et al. |
| 2010/0049194 A1 | 2/2010 | Hart et al. |
| 2010/0057078 A1 | 3/2010 | Arts et al. |
| 2010/0057081 A1 | 3/2010 | Hanna |
| 2010/0057082 A1 | 3/2010 | Hanna |
| 2010/0057083 A1 | 3/2010 | Hanna |
| 2010/0057084 A1 | 3/2010 | Hanna |
| 2010/0063500 A1 | 3/2010 | Muszala |
| 2010/0069903 A1 | 3/2010 | Allen, IV et al. |
| 2010/0069904 A1 | 3/2010 | Cunningham |
| 2010/0069953 A1 | 3/2010 | Cunningham et al. |
| 2010/0076427 A1 | 3/2010 | Heard |
| 2010/0076430 A1 | 3/2010 | Romero |
| 2010/0076431 A1 | 3/2010 | Allen, IV |
| 2010/0076432 A1 | 3/2010 | Horner |
| 2010/0087816 A1 | 4/2010 | Roy |

(56) References Cited

U.S. PATENT DOCUMENTS

| | | |
|---|---|---|
| 2010/0087818 A1 | 4/2010 | Cunningham |
| 2010/0094271 A1 | 4/2010 | Ward et al. |
| 2010/0094286 A1 | 4/2010 | Chojin |
| 2010/0094287 A1 | 4/2010 | Cunningham et al. |
| 2010/0094289 A1 | 4/2010 | Taylor et al. |
| 2010/0100122 A1 | 4/2010 | Hinton |
| 2010/0130971 A1 | 5/2010 | Baily |
| 2010/0130977 A1 | 5/2010 | Garrison et al. |
| 2010/0145334 A1 | 6/2010 | Olson et al. |
| 2010/0179539 A1 | 7/2010 | Nau, Jr. |
| 2010/0179543 A1 | 7/2010 | Johnson et al. |
| 2010/0179545 A1 | 7/2010 | Twomey et al. |
| 2010/0179546 A1 | 7/2010 | Cunningham |
| 2010/0179547 A1 | 7/2010 | Cunningham et al. |
| 2010/0198215 A1 | 8/2010 | Julian et al. |
| 2010/0198218 A1 | 8/2010 | Manzo |
| 2010/0198248 A1 | 8/2010 | Vakharia |
| 2010/0204697 A1 | 8/2010 | Dumbauld et al. |
| 2010/0204698 A1 | 8/2010 | Chapman et al. |
| 2010/0217258 A1 | 8/2010 | Floume et al. |
| 2010/0217264 A1 | 8/2010 | Odom et al. |
| 2010/0228249 A1 | 9/2010 | Mohr et al. |
| 2010/0228250 A1 | 9/2010 | Brogna |
| 2010/0249769 A1 | 9/2010 | Nau, Jr. et al. |
| 2010/0249776 A1 | 9/2010 | Kerr |
| 2010/0256635 A1 | 10/2010 | McKenna et al. |
| 2010/0274160 A1 | 10/2010 | Yachi et al. |
| 2010/0274244 A1 | 10/2010 | Heard |
| 2010/0274265 A1 | 10/2010 | Wingardner et al. |
| 2010/0280511 A1 | 11/2010 | Rachlin et al. |
| 2010/0280515 A1 | 11/2010 | Hixson et al. |
| 2010/0286691 A1 | 11/2010 | Kerr et al. |
| 2010/0292691 A1 | 11/2010 | Brogna |
| 2010/0307934 A1 | 12/2010 | Chowaniec et al. |
| 2010/0312235 A1 | 12/2010 | Bahney |
| 2010/0312238 A1 | 12/2010 | Schechter et al. |
| 2010/0312242 A1 | 12/2010 | Odom |
| 2010/0331742 A1 | 12/2010 | Masuda |
| 2010/0331839 A1 | 12/2010 | Schechter et al. |
| 2011/0004209 A1 | 1/2011 | Lawes et al. |
| 2011/0004210 A1 | 1/2011 | Johnson et al. |
| 2011/0009864 A1 | 1/2011 | Bucciaglia et al. |
| 2011/0015632 A1 | 1/2011 | Artale |
| 2011/0018164 A1 | 1/2011 | Sartor et al. |
| 2011/0034918 A1 | 2/2011 | Reschke |
| 2011/0036183 A1 | 2/2011 | Artale et al. |
| 2011/0046623 A1 | 2/2011 | Reschke |
| 2011/0054467 A1 | 3/2011 | Mueller et al. |
| 2011/0054468 A1 | 3/2011 | Dycus |
| 2011/0054469 A1 | 3/2011 | Kappus et al. |
| 2011/0054471 A1 | 3/2011 | Gerhardt et al. |
| 2011/0054472 A1 | 3/2011 | Romero |
| 2011/0060333 A1 | 3/2011 | Mueller |
| 2011/0060334 A1 | 3/2011 | Brandt et al. |
| 2011/0060335 A1 | 3/2011 | Harper et al. |
| 2011/0060356 A1 | 3/2011 | Reschke et al. |
| 2011/0066174 A1 | 3/2011 | Gilbert |
| 2011/0071522 A1 | 3/2011 | Dumbauld et al. |
| 2011/0071523 A1 | 3/2011 | Dickhans |
| 2011/0071525 A1 | 3/2011 | Dumbauld et al. |
| 2011/0072638 A1 | 3/2011 | Brandt et al. |
| 2011/0073246 A1 | 3/2011 | Brandt et al. |
| 2011/0073594 A1 | 3/2011 | Bonn |
| 2011/0077648 A1 | 3/2011 | Lee et al. |
| 2011/0077649 A1 | 3/2011 | Kingsley |
| 2011/0082457 A1 | 4/2011 | Kerr et al. |
| 2011/0082494 A1 | 4/2011 | Kerr et al. |
| 2011/0087221 A1 | 4/2011 | Siebrecht et al. |
| 2011/0098689 A1 | 4/2011 | Nau, Jr. et al. |
| 2011/0106079 A1 | 5/2011 | Garrison et al. |
| 2011/0118736 A1 | 5/2011 | Harper et al. |
| 2011/0162796 A1 | 7/2011 | Guerra |
| 2011/0178519 A1 | 7/2011 | Couture et al. |
| 2011/0184405 A1 | 7/2011 | Mueller |
| 2011/0190653 A1 | 8/2011 | Harper et al. |
| 2011/0190765 A1 | 8/2011 | Chojin |
| 2011/0193608 A1 | 8/2011 | Krapohl |
| 2011/0218530 A1 | 9/2011 | Reschke |
| 2011/0230880 A1 | 9/2011 | Chojin et al. |
| 2011/0238066 A1 | 9/2011 | Olson |
| 2011/0238067 A1 | 9/2011 | Moses et al. |
| 2011/0251605 A1 | 10/2011 | Hoarau et al. |
| 2011/0251606 A1 | 10/2011 | Kerr |
| 2011/0251611 A1 | 10/2011 | Horner et al. |
| 2011/0270245 A1 | 11/2011 | Horner et al. |
| 2011/0270250 A1 | 11/2011 | Horner et al. |
| 2011/0270251 A1 | 11/2011 | Horner et al. |
| 2011/0270252 A1 | 11/2011 | Horner et al. |
| 2011/0276048 A1 | 11/2011 | Kerr et al. |
| 2011/0276049 A1 | 11/2011 | Gerhardt |
| 2011/0295251 A1 | 12/2011 | Garrison |
| 2011/0295313 A1 | 12/2011 | Kerr |
| 2011/0301592 A1 | 12/2011 | Kerr et al. |
| 2011/0301599 A1 | 12/2011 | Roy et al. |
| 2011/0301600 A1 | 12/2011 | Garrison et al. |
| 2011/0301601 A1 | 12/2011 | Garrison et al. |
| 2011/0301602 A1 | 12/2011 | Roy et al. |
| 2011/0301603 A1 | 12/2011 | Kerr et al. |
| 2011/0301604 A1 | 12/2011 | Horner et al. |
| 2011/0301605 A1 | 12/2011 | Horner |
| 2011/0301606 A1 | 12/2011 | Kerr |
| 2011/0301637 A1 | 12/2011 | Kerr et al. |
| 2011/0319886 A1 | 12/2011 | Chojin et al. |
| 2011/0319888 A1 | 12/2011 | Mueller et al. |
| 2012/0004658 A1 | 1/2012 | Chojin |
| 2012/0010614 A1 | 1/2012 | Couture |
| 2012/0022532 A1 | 1/2012 | Garrison |
| 2012/0029515 A1 | 2/2012 | Couture |
| 2012/0041438 A1 | 2/2012 | Nau, Jr. et al. |
| 2012/0046659 A1 | 2/2012 | Mueller |
| 2012/0046660 A1 | 2/2012 | Nau, Jr. |
| 2012/0046662 A1 | 2/2012 | Gilbert |
| 2012/0059371 A1 | 3/2012 | Anderson et al. |
| 2012/0059372 A1 | 3/2012 | Johnson |
| 2012/0059374 A1 | 3/2012 | Johnson et al. |
| 2012/0059375 A1 | 3/2012 | Couture et al. |
| 2012/0059408 A1 | 3/2012 | Mueller |
| 2012/0059409 A1 | 3/2012 | Reschke et al. |
| 2012/0078250 A1 | 3/2012 | Orton et al. |
| 2012/0083785 A1 | 4/2012 | Roy et al. |
| 2012/0083786 A1 | 4/2012 | Artale et al. |
| 2012/0083827 A1 | 4/2012 | Artale et al. |
| 2012/0095456 A1 | 4/2012 | Schechter et al. |
| 2012/0095460 A1 | 4/2012 | Rooks et al. |
| 2012/0123404 A1 | 5/2012 | Craig |
| 2012/0172868 A1 | 7/2012 | Twomey et al. |
| 2012/0209263 A1 | 8/2012 | Sharp et al. |
| 2012/0239034 A1 | 9/2012 | Horner et al. |
| 2012/0265241 A1 | 10/2012 | Hart et al. |
| 2012/0296205 A1 | 11/2012 | Chernov et al. |
| 2012/0296238 A1 | 11/2012 | Chernov et al. |
| 2012/0330308 A1 | 12/2012 | Joseph |
| 2013/0018364 A1 | 1/2013 | Chernov et al. |
| 2013/0022495 A1 | 1/2013 | Allen, IV et al. |
| 2013/0071282 A1 | 3/2013 | Fry |
| 2013/0079774 A1 | 3/2013 | Whitney et al. |

FOREIGN PATENT DOCUMENTS

| | | |
|---|---|---|
| EP | 0572131 A1 | 12/1993 |
| EP | 0584787 A1 | 3/1994 |
| EP | 0589555 A1 | 3/1994 |
| EP | 0589453 A3 | 4/1994 |
| EP | 0648475 A1 | 4/1995 |
| EP | 0624348 A3 | 6/1995 |
| EP | 0517243 B1 | 9/1997 |
| EP | 0541930 B1 | 3/1998 |
| EP | 0853922 A1 | 7/1998 |
| EP | 0878169 A1 | 11/1998 |
| EP | 0623316 B1 | 3/1999 |
| EP | 0650701 B1 | 3/1999 |
| EP | 0923907 A1 | 6/1999 |
| EP | 0640317 B1 | 9/1999 |
| EP | 0950378 A1 | 10/1999 |

(56) References Cited

FOREIGN PATENT DOCUMENTS

| | | |
|---|---|---|
| EP | 0986990 A1 | 3/2000 |
| EP | 1034747 A1 | 9/2000 |
| EP | 1034748 A1 | 9/2000 |
| EP | 0694290 B1 | 11/2000 |
| EP | 1050278 A1 | 11/2000 |
| EP | 1053719 A1 | 11/2000 |
| EP | 1053720 A1 | 11/2000 |
| EP | 1055399 A1 | 11/2000 |
| EP | 1055400 A1 | 11/2000 |
| EP | 1080694 A1 | 3/2001 |
| EP | 1082944 A1 | 3/2001 |
| EP | 1177771 A1 | 2/2002 |
| EP | 1186274 A2 | 3/2002 |
| EP | 1201192 A1 | 5/2002 |
| EP | 1278007 A1 | 1/2003 |
| EP | 0717966 B1 | 4/2003 |
| EP | 1301135 A1 | 4/2003 |
| EP | 0887046 B1 | 7/2003 |
| EP | 1330991 A1 | 7/2003 |
| EP | 0913126 B1 | 10/2004 |
| EP | 1472984 A1 | 11/2004 |
| EP | 0754437 B2 | 12/2004 |
| EP | 0888747 B1 | 12/2004 |
| EP | 1025807 B1 | 12/2004 |
| EP | 1486177 A2 | 12/2004 |
| EP | 0774232 B1 | 1/2005 |
| EP | 1527744 A1 | 5/2005 |
| EP | 1527747 A2 | 5/2005 |
| EP | 1530952 A1 | 5/2005 |
| EP | 1532932 A1 | 5/2005 |
| EP | 1535581 A2 | 6/2005 |
| EP | 1545360 A1 | 6/2005 |
| EP | 1609430 A1 | 12/2005 |
| EP | 1034746 B1 | 3/2006 |
| EP | 1628586 A2 | 3/2006 |
| EP | 1632192 A1 | 3/2006 |
| EP | 1642543 A1 | 4/2006 |
| EP | 1645238 A1 | 4/2006 |
| EP | 1645240 A2 | 4/2006 |
| EP | 1649821 A1 | 4/2006 |
| EP | 0875209 B1 | 5/2006 |
| EP | 1683496 A2 | 7/2006 |
| EP | 1707143 A1 | 10/2006 |
| EP | 1767163 A1 | 3/2007 |
| EP | 1769765 A1 | 4/2007 |
| EP | 1769766 A1 | 4/2007 |
| EP | 1772109 A1 | 4/2007 |
| EP | 1785097 A2 | 5/2007 |
| EP | 1785098 A2 | 5/2007 |
| EP | 1785101 A2 | 5/2007 |
| EP | 1787597 A1 | 5/2007 |
| EP | 1810625 A1 | 7/2007 |
| EP | 1810628 A1 | 7/2007 |
| EP | 1842500 A2 | 10/2007 |
| EP | 1878400 A1 | 1/2008 |
| EP | 1894535 A2 | 3/2008 |
| EP | 1920725 A2 | 5/2008 |
| EP | 1929970 A1 | 6/2008 |
| EP | 1946715 A1 | 7/2008 |
| EP | 1958583 A2 | 8/2008 |
| EP | 1990019 A2 | 11/2008 |
| EP | 1997438 A2 | 12/2008 |
| EP | 1997439 A2 | 12/2008 |
| EP | 2103268 A1 | 9/2009 |
| EP | 2105104 A2 | 9/2009 |
| EP | 2147649 A1 | 1/2010 |
| EP | 2153791 A1 | 2/2010 |
| EP | 2206474 A2 | 7/2010 |
| EP | 2243439 A1 | 10/2010 |
| EP | 2294998 A1 | 3/2011 |
| EP | 2301467 A1 | 3/2011 |
| JP | 6502328 | 3/1992 |
| JP | 6121797 A | 5/1994 |
| JP | 6285078 A | 10/1994 |
| JP | 6511401 A | 12/1994 |
| JP | 08056955 | 5/1996 |
| JP | 8289895 A | 11/1996 |
| JP | 8317934 A | 12/1996 |
| JP | 8317936 A | 12/1996 |
| JP | 910223 A | 1/1997 |
| JP | 9122138 A | 5/1997 |
| JP | 1024051 A | 1/1998 |
| JP | 10155798 A | 6/1998 |
| JP | 1147150 A | 2/1999 |
| JP | 11070124 A | 3/1999 |
| JP | 11169381 A | 6/1999 |
| JP | 11192238 A | 7/1999 |
| JP | 2000102545 A | 4/2000 |
| JP | 2001003400 A | 1/2001 |
| JP | 2001008944 | 1/2001 |
| JP | 2001029356 | 2/2001 |
| JP | 2001190564 A | 7/2001 |
| JP | 2002528166 A | 9/2002 |
| JP | 2003245285 A | 9/2003 |
| JP | 2004517668 A | 6/2004 |
| JP | 2004528869 A | 9/2004 |
| JP | 2011125195 A | 6/2011 |
| JP | 0006030945 B2 | 11/2016 |
| WO | 8900757 A1 | 1/1989 |
| WO | 9204873 A1 | 4/1992 |
| WO | 9206642 A1 | 4/1992 |
| WO | 9319681 A1 | 10/1993 |
| WO | 9321845 A1 | 11/1993 |
| WO | 9400059 A1 | 1/1994 |
| WO | 9408524 A1 | 4/1994 |
| WO | 9420025 A1 | 9/1994 |
| WO | 9502369 A1 | 1/1995 |
| WO | 9507662 A1 | 3/1995 |
| WO | 9515124 A1 | 6/1995 |
| WO | 9520360 A1 | 8/1995 |
| WO | 9520921 A1 | 8/1995 |
| WO | 9605776 A1 | 2/1996 |
| WO | 9611635 A1 | 4/1996 |
| WO | 9613218 A1 | 5/1996 |
| WO | 9622056 A1 | 7/1996 |
| WO | 9700646 A1 | 1/1997 |
| WO | 9700647 A1 | 1/1997 |
| WO | 9710764 A1 | 3/1997 |
| WO | 9718768 A1 | 5/1997 |
| WO | 9724073 A1 | 7/1997 |
| WO | 9724993 A1 | 7/1997 |
| WO | 9814124 A1 | 4/1998 |
| WO | 9827880 A1 | 7/1998 |
| WO | 9831290 A1 | 7/1998 |
| WO | 9843264 A1 | 10/1998 |
| WO | 9903407 A1 | 1/1999 |
| WO | 9903408 A1 | 1/1999 |
| WO | 9903409 A1 | 1/1999 |
| WO | 9903414 A1 | 1/1999 |
| WO | 9912488 A1 | 3/1999 |
| WO | 9923933 A2 | 5/1999 |
| WO | 9923959 A1 | 5/1999 |
| WO | 9925261 A1 | 5/1999 |
| WO | 9940857 A1 | 8/1999 |
| WO | 9940861 A1 | 8/1999 |
| WO | 9951158 A1 | 10/1999 |
| WO | 9966850 A1 | 12/1999 |
| WO | 0024322 A1 | 5/2000 |
| WO | 0024330 A1 | 5/2000 |
| WO | 0024331 A1 | 5/2000 |
| WO | 0033753 A1 | 6/2000 |
| WO | 0036986 A1 | 6/2000 |
| WO | 0041638 A1 | 7/2000 |
| WO | 0047124 A1 | 8/2000 |
| WO | 0053112 A2 | 9/2000 |
| WO | 0059392 A1 | 10/2000 |
| WO | 0101847 A1 | 1/2001 |
| WO | 0115614 A1 | 3/2001 |
| WO | 0117448 A2 | 3/2001 |
| WO | 0154604 A1 | 8/2001 |
| WO | 0166025 A1 | 9/2001 |
| WO | 0207627 | 1/2002 |
| WO | 02058544 A2 | 8/2002 |
| WO | 02067798 A1 | 9/2002 |

(56) References Cited

FOREIGN PATENT DOCUMENTS

| | | |
|---|---|---|
| WO | 02080783 A1 | 10/2002 |
| WO | 02080784 A1 | 10/2002 |
| WO | 02080785 A1 | 10/2002 |
| WO | 02080786 A1 | 10/2002 |
| WO | 02080793 A1 | 10/2002 |
| WO | 02080794 A1 | 10/2002 |
| WO | 02080795 A1 | 10/2002 |
| WO | 02080796 A1 | 10/2002 |
| WO | 02080797 A1 | 10/2002 |
| WO | 02080798 A1 | 10/2002 |
| WO | 02080799 A1 | 10/2002 |
| WO | 02081170 A1 | 10/2002 |
| WO | 02085218 A2 | 10/2002 |
| WO | 03061500 A2 | 7/2003 |
| WO | 03068046 A2 | 8/2003 |
| WO | 03090630 A2 | 11/2003 |
| WO | 03096880 A2 | 11/2003 |
| WO | 03101311 A1 | 12/2003 |
| WO | 2004028585 A2 | 4/2004 |
| WO | 2004032776 A1 | 4/2004 |
| WO | 2004032777 A1 | 4/2004 |
| WO | 2004052221 A1 | 6/2004 |
| WO | 2004073488 A2 | 9/2004 |
| WO | 2004073490 A2 | 9/2004 |
| WO | 2004073753 A2 | 9/2004 |
| WO | 2004082495 A1 | 9/2004 |
| WO | 2004098383 A2 | 11/2004 |
| WO | 2004103156 A2 | 12/2004 |
| WO | 2005004734 A1 | 1/2005 |
| WO | 2005004735 A1 | 1/2005 |
| WO | 2005009255 A1 | 2/2005 |
| WO | 2005011049 A2 | 2/2005 |
| WO | 2005030071 A1 | 4/2005 |
| WO | 2005048809 A1 | 6/2005 |
| WO | 2005050151 A1 | 6/2005 |
| WO | 2006021269 A1 | 3/2006 |
| WO | 2005110264 A2 | 4/2006 |
| WO | 2008008457 A2 | 1/2008 |
| WO | 2008040483 A1 | 4/2008 |
| WO | 2008045348 A2 | 4/2008 |
| WO | 2008045350 A2 | 4/2008 |
| WO | 20080112147 A1 | 9/2008 |
| WO | 20090005850 A1 | 1/2009 |
| WO | 2009032623 A2 | 3/2009 |
| WO | 2009039179 A1 | 3/2009 |
| WO | 2009039510 A1 | 3/2009 |
| WO | 2009124097 A1 | 10/2009 |
| WO | 2010104753 A1 | 9/2010 |

OTHER PUBLICATIONS

Burdette et al. "In Vivo Probe Measurement Technique for Determining Dielectric Properties at VHF Through Microwave Frequencies", IEEE Transactions on Microwave Theory and Techniques, vol. MTT-28, No. 4, Apr. 1980 pp. 414-427.
LigaSure Vessel Sealing System, the Seal of Confidence in General, Gynecologic, Urologic, and Laparaoscopic Surgery; Sales/Product Literature; Apr. 2002.
Benaron et al., "Optical Time-Of-Flight and Absorbance Imaging of Biologic Media", Science, American Association for the Advancement of Science, Washington, DC, vol. 259, Mar. 5, 1993, pp. 1463-1466.
Int'l Search Report EP 98957773 dated Aug. 1, 2001.
Int'l Search Report EP 04709033.7 dated Dec. 8, 2010.
Int'l Search Report EP 05013894 dated Feb. 3, 2006.
Int'l Search Report EP 05020532 dated Jan. 10, 2006.
Int'l Search Report EP 07 004429.2 dated Nov. 2, 2010.
Int'l Search Report EP 07 016911 dated May 28, 2010.
Int'l Search Report EP 07 016911.5 extended dated Mar. 2, 2011.
Int'l Search Report EP 07 021646.0 dated Mar. 20, 2008.
Int'l Search Report EP 08 020807.7 dated Apr. 24, 2009.
Int'l Search Report PCT/US08/61498 dated Sep. 22, 2008.
Int'l Search Report PCT/US09/032690 dated Jun. 16, 2009.
U.S. Appl. No. 08/926,869, filed Sep. 10, 1997, James G. Chandler.
U.S. Appl. No. 09/177,950, filed Oct. 23, 1998, Randel A. Frazier.
U.S. Appl. No. 09/387,883, filed Sep. 1, 1999, Dale F. Schmaltz.
U.S. Appl. No. 09/591,328, filed Jun. 9, 2000, Thomas P. Ryan.
Int'l Search Report EP 11 180182.5 dated Nov. 15, 2011.
Int'l Search Report PCT/US03/08146 dated Aug. 8, 2003.
Int'l Search Report PCT/US03/18674 dated Sep. 18, 2003.
Int'l Search Report PCT/US03/18676 dated Sep. 19, 2003.
Int'l Search Report PCT/US03/28539 dated Jan. 6, 2004.
Int'l Search Report PCT/USO4/03436 dated Mar. 3, 2005.
Int'l Search Report PCT/USO4/13273 dated Dec. 15, 2004.
Int'l Search Report PCT/US08/52460 dated Apr. 24, 2008.
Koyle et al., "Laparoscopic Palomo Varicocele Ligation in Children and Adolescents" Pediatric Endosurgery & Innovative Techniques, vol. 6, No. 1, 2002.
W. Scott Helton, "LigaSure Vessel Sealing System: Revolutionary Hemostasis Product for General Surgery"; Sales/Product Literature 1999.
LigaSure Vessel Sealing System, the Seal of Confidence in General, Gynecologic, Urologic, and Laparabscopic Surgery; Sales/Product Literature; Apr. 2002.
Joseph Ortenberg "LigaSure System Used in Laparoscopic 1st and 2nd Stage Orchiopexy" Innovations That Work, Nov. 2002.
Sigel et al., "The Mechanism of Blood Vessel Closure by High Frequency Electrocoagulation" Surgery Gynecology & Obstetrics, Oct. 1965 pp. 823-831.
Sampayan et al, "Multilayer Ultra-High Gradient Insulator Technology" Discharges and Electrical Insulation in Vacuum, 1998. Netherlands Aug. 17-21, 1998; vol. 2, pp. 740-743.
Paul G. Horgan, "A Novel Technique for Parenchymal Division During Hepatectomy" The American Journal of Surgery, vol. 181, No. 3, Apr. 2001 pp. 236-237.
Olsson et al. "Radical Cystectomy in Females". Current Surgical Techniques in Urology, vol. 14, Issue 3, 2001.
Palazzo et al. "Randomized clinical trial of Ligasure versus open haemorrhoidectomy" British Journal of Surgery 2002, 89, 154-157.
Levy et al. "Randomized Trial of Suture Versus Electrosurgical Bipolar Vessel Sealing in Vaginal Hysterectomy" Obstetrics & Gynecology, vol. 102, No. 1, Jul. 2003.
"Reducing Needlestick Injuries in the Operating Room"; Sales/Product Literature 2001.
Bergdahl et al., "Studies on Coagulation and the Development of an Automatic Computerized Bipolar Coagulator" J. Neurosurg, vol. 75, Jul. 1991, pp. 148-151.
Strasberg et al. "A Phase I Study of the LigaSure Vessel Sealing System in Hepatic Surgery" Section of HPB Surger, Washington University School of Medicine, St. Louis MO, Presented at AHPBA, Feb. 2001.
Sayfan et al., "Sutureless Closed Hemorrhoidectomy: A New Technique" Annals of Surgery, vol. 234, No. 1, Jul. 2001, pp. 21-24.
Levy et al., "Update on Hysterectomy—New Technologies and Techniques" OBG Management, Feb. 2003.
Dulemba et al. "Use of a Bipolar Electrothermal Vessel Sealer in Laparoscopically Assisted Vaginal Hysterectomy" Sales/Product Literature; Jan. 2004.
Strasberg et al., "Use of a Bipolar Vessel-Sealing Device for Parenchymal Transection During Liver Surgery" Journal of Gastrointestinal Surgery, vol. 6, No. 4, Jul./Aug. 2002 pp. 569-574.
Sengupta et al., "Use of a Computer-Controlled Bipolar Diathermy System in Radical Prostatectomies and Other Open Urological Surgery" ANZ Journal of Surgery (2001)71.9 pp. 538-540.
Rothenberg et al. "Use of the LigaSure Vessel Sealing System in Minimally Invasive Surgery in Children" Int'l Pediatric Endosurgery Group (IPEG) 2000.
Crawford et al. "Use of the LigaSure Vessel Sealing System in Urologic Cancer Surge" Grand Rounds in Urology 1999 vol. 1 Issue 4 pp. 10-17.
Craig Johnson, "Use of the LigaSure Vessel Sealing System in Bloodless Hemorrhoidectomy"; Innovations That Work, Mar. 2000.
Levy et al. "Use of a New Energy-based Vessel Ligation Device During Vaginal Hysterectomy"; Int'l Federation of Gynecology and Obstetrics (FIGO) World Congress 1999.

(56) References Cited

OTHER PUBLICATIONS

Barbara Levy, "Use of a New Vessel Ligation Device During Vaginal Hysterectomy" FIGO 2000, Washington, D.C.
E. David Crawford, "Use of a Novel Vessel Sealing Technology in Management of the Dorsal Veinous Complex" Sales/Product Literature 2000.
Jarrett et al., "Use of the LigaSure Vessel Sealing System for Peri-Hilar Vessels in Laparoscopic Nephrectomy"; Sales/Product Literature 2000.
Crouch et al. "A Velocity-Dependent Model for Needle Insertion in Soft Tissue"; MICCAI 2005; LNCS 3750 pp. 624-632, Dated: 2005.
McLellan et al., "Vessel Sealing for Hemostasis During Pelvic Surgery" Int'l Federation of Gynecology and Obstetrics FIGO World Congress 2000, Washington, DC.
McLellan et al. "Vessel Sealing for Hemostasis During Gynecologic Surgery" Sales/Product Literature 1999.
Int'l Search Report EP 98944778.4 dated Oct. 31, 2000.
Int'l Search Report EP 98957771 dated Aug. 9, 2001.
Int'l Search Report EP 98958575.7 dated Sep. 20, 2002.
Int'l Search Report EP 04013772.1 dated Apr. 1, 2005.
Int'l Search Report EP 04027314.6 dated Mar. 10, 2005.
Int'l Search Report EP 04027479.7 dated Mar. 8, 2005.
Int'l Search Report EP 04027705.5 dated Feb. 3, 2005.
Int'l Search Report EP 04752343.6 dated Jul. 20, 2007.
Int'l Search Report EP 05002671.5 dated Dec. 22, 2008.
Int'l Search Report EP 05002674.9 dated Jan. 16, 2009.
Int'l Search Report EP 05013463.4 dated Oct. 7, 2005.
Int'l Search Report EP 05013895.7 dated Oct. 21, 2005.
Int'l Search Report EP 05016399.7 dated Jan. 13, 2006.
Intl Search Report EP 05017281.6 dated Nov. 24, 2005.
Int'l Search Report EP 05019130.3 dated Oct. 27, 2005.
Int'l Search Report EP 05019429.9 dated May 6, 2008.
Int'l Search Report EP 05020665.5 dated Feb. 27, 2006.
Int'l Search Report EP 05020666.3 dated Feb. 27, 2006.
Int'l Search Report EP 05021197.8 dated Feb. 20, 2006.
Int'l Search Report EP 05021779.3 dated Feb. 2, 2006.
Int'l Search Report EP 05021780.1 dated Feb. 23, 2006.
Int'l Search Report EP 05021937.7 dated Jan. 23, 2006.
Int'l Search Report—extended—EP 05021937.7 dated Mar. 15, 2006.
Int'l Search Report EP 05023017.6 dated Feb. 24, 2006.
Int'l Search Report EP 06002279.5 dated Mar. 30, 2006.
Int'l Search Report EP 06005185.1 dated May 10, 2006.
Int'l Search Report EP 06006716.2 dated Aug. 4, 2006.
Int'l Search Report EP 06008515.6 dated Jan. 8, 2009.
Int'l Search Report EP 06008779.8 dated Jul. 13, 2006.
Int'l Search Report EP 06014461.5 dated Oct. 31, 2006.
Int'l Search Report EP 06020574.7 dated Oct. 2, 2007.
Int'l Search Report EP 06020583.8 dated Feb. 7, 2007.
Int'l Search Report EP 06020584.6 dated Feb. 1, 2007.
Int'l Search Report EP 06020756.0 dated Feb. 16, 2007.
Int'l Search Report EP 06 024122.1 dated Apr. 16, 2007.
Int'l Search Report EP 06024123.9 dated Mar. 6, 2007.
Int'l Search Report EP 07 001480.8 dated Apr. 19, 2007.
Int'l Search Report EP 07 001488.1 dated Jun. 5, 2007.
Int'l Search Report EP 07 009026.1 dated Oct. 8, 2007.
Int'l Search Report Extended—EP 07 009029.5 dated Jul. 20, 2007.
Int'l Search Report EP 07 009321.6 dated Aug. 28, 2007.
Int'l Search Report EP 07 010672.9 dated Oct. 16, 2007.
Int'l Search Report EP 07 013779.9 dated Oct. 26, 2007.
Int'l Search Report EP 07 014016 dated Jan. 28, 2008.
Int'l Search Report EP 07 015191.5 dated Jan. 23, 2008.
Int'l Search Report EP 07 015601.3 dated Jan. 4, 2008.
Int'l Search Report EP 07 020283.3 dated Feb. 5, 2008.
Int'l Search Report EP 07 021646.0 dated Jul. 9, 2008.
Int'l Search Report EP 07 021647.8 dated May 2, 2008.
Int'l Search Report EP 08 002692.5 dated Dec. 12, 2008.
Int'l Search Report EP 08 004655.0 dated Jun. 24, 2008.
Int'l Search Report EP 08 006732.5 dated Jul. 29, 2008.
Int'l Search Report EP 08 006917.2 dated Jul. 3, 2008.
Int'l Search Report EP 08 016539.2 dated Jan. 8, 2009.
Int'l Search Report EP 09 152267.2 dated Jun. 15, 2009.
Int'l Search Report EP 09 152898.4 dated Jun. 10, 2009.
Int'l Search Report PCT/US98/18640 dated Jan. 29, 1999.
Int'l Search Report PCT/US98/23950 dated Jan. 14, 1999.
Int'l Search Report PCT/US98/24281 dated Feb. 22, 1999.
Int'l Search Report PCT/US99/24869 dated Feb. 3, 2000.
Int'l Search Report PCT/US01/11218 dated Aug. 14, 2001.
Int'l Search Report PCT/US01/11224 dated Nov. 13, 2001.
Int'l Search Report PCT/US01/11340 dated Aug. 16, 2001.
Int'l Search Report PCT/US01/11420 dated Oct. 16, 2001.
Int'l Search Report PCT/US02/01890 dated Jul. 25, 2002.
Int'l Search Report PCT/US02/11100 dated Jul. 16, 2002.
Int'l Search Report PCT/US03/28534 dated Dec. 19, 2003.
Int'l Search Report PCT/US04/03436 dated Mar. 3, 2005.
Int'l Search Report PCT/US04/13273 dated Dec. 15, 2004.
Int'l Search Report PCT/US04/15311 dated Jan. 12, 2005.
Int'l Search Report PCT/US07/021438 dated Apr. 1, 2008.
Int'l Search Report PCT/US07/021440 dated Apr. 8, 2008.
Int'l Search Report EP 09 003677.3 dated May 4, 2009.
Int'l Search Report EP 09 003813.4 dated Aug. 3, 2009.
Int'l Search Report EP 09 004491.8 dated Sep. 9, 2009.
Int'l Search Report EP 09 005051.9 dated Jul. 6, 2009.
Int'l Search Report EP 09 005575.7 dated Sep. 9, 2009.
Int'l Search Report EP 09 010521.4 dated Dec. 16, 2009.
Int'l Search Report EP 09 011745.8 dated Jan. 5, 2010.
Int'l Search Report EP 09 012629.3 dated Dec. 8, 2009.
Int'l Search Report EP 09 012687.1 dated Dec. 23, 2009.
Int'l Search Report EP 09 012688.9 dated Dec. 28, 2009.
Int'l Search Report EP 09 154850.3 dated Jul. 20, 2009.
Int'l Search Report EP 09 160476.9 dated Aug. 4, 2009.
Int'l Search Report EP 09 164903.8 dated Aug. 21, 2009.
Int'l Search Report EP 09 165753.6 dated Nov. 11, 2009.
Int'l Search Report EP 09 168153.6 dated Jan. 14, 2010.
Int'l Search Report EP 09 168810.1 dated Feb. 2, 2010.
Int'l Search Report EP 09 172749.5 dated Dec. 4, 2009.
Int'l Search Report EP 10 000259.1 dated Jun. 30, 2010.
Int'l Search Report EP 10 011750.6 dated Feb. 1, 2011.
Int'l Search Report EP 10 157500.9 dated Jul. 30, 2010.
Int'l Search Report EP 10 159205.3 dated Jul. 7, 2010.
Int'l Search Report EP 10 160870,1 dated Aug. 9, 2010.
Int'l Search Report EP 10 161596.1 dated Jul. 28, 2010.
U.S. Appl. No. 15/689,808, filed Aug. 29, 2017, Patented, U.S. Pat. No. 10,188,454.
U.S. Appl. No. 15/049,632, filed Feb. 22, 2016, Patented, U.S. Pat. No. 9,750,561.
U.S. Appl. No. 14/557,767, filed Dec. 2, 2014, Patented, U.S. Pat. No. 9,265,552.
U.S. Appl. No. 13/358,657, filed Jan. 26, 2012, Patented, U.S. Pat. No. 8,898,888.
U.S. Appl. No. 12/568,282, filed Sep. 28, 2009, Patented, U.S. Appl. No. 8,112,871.
Int'l Search Report EP 10 167655.9 dated Aug. 31, 2011.
Int'l Search Report EP 10 168705.1 dated Oct. 4, 2010.
Int'l Search Report EP 10.169647.4 dated Oct. 29, 2010.
Int'l Search Report EP 10 172005.0 dated Sep. 30, 2010.
Int'l Search Report EP 10 175956.1 dated Nov. 12, 2010.
Int'l Search Report EP 10 181034.9 dated Jan. 26, 2011.
Int'l Search Report EP 10 181575.1 dated Apr. 5, 2011.
Int'l Search Report EP 10 181969.6 dated Feb. 4, 2011.
Int'l Search Report EP 10 182019 dated Aug. 4, 2011.
Int'l Search Report EP 10 182022.3 dated Mar. 11, 2011.
Int'l Search Report EP 10 185386.9 dated Jan. 10, 2011.
Int'l Search Report EP 10 185405.7 dated Jan. 5, 2011.
Int'l Search Report EP 10 186527.7 dated Jun. 17, 2011.
Int'l Search Report EP 10 189206.5 dated Mar. 17, 2011.
Int'l Search Report EP 10 191320.0 dated Feb. 15, 2011.
Int'l Search Report EP 11 151509.4 dated Jun. 6, 2011.
Int'l Search Report EP 11 152220.7 dated May 19, 2011.
Int'l Search Report EP 11 152360.1 dated Jun. 6, 2011.
Int'l Search Report EP 11 159771.2 dated May 28, 2010.
Int'l Search Report EP 11 161117.4 dated Jun. 30, 2011.
Int'l Search Report EP 11 161118.2 dated Oct. 12, 2011.

(56) References Cited

OTHER PUBLICATIONS

Int'l Search Report EP 11 164274.0 dated Aug. 3, 2011.
Int'l Search Report EP 11 164275.7 dated Aug. 25, 2011.
Int'l Search Report EP 11 167437.0 dated Aug. 8, 2011.
Int'l Search Report EP 11 168458.5 dated Jul. 29, 2011.
Int'l Search Report EP 11 173008.1 dated Nov. 4, 2011.
Int'l Search Report EP 11 179514 dated Nov. 4, 2011.

\* cited by examiner

ELECTROSURGICAL SEAL PLATES

CROSS-REFERENCE TO RELATED APPLICATIONS

The present application is a continuation application of U.S. patent application Ser. No. 15/689,808, filed on Aug. 29, 2017, now U.S. Pat. No. 10,188,454, which is a continuation application of U.S. patent application Ser. No. 15/049,632, filed on Feb. 22, 2016, now U.S. Pat. No. 9,750,561, which is a continuation application of U.S. patent application Ser. No. 14/557,767, filed on Dec. 2, 2014, now U.S. Pat. No. 9,265,552, which is a continuation application of U.S. patent application Ser. No. 13/358,657, filed on Jan. 26, 2012, now U.S. Pat. No. 8,898,888, which is a divisional application of U.S. patent application Ser. No. 12/568,282, filed on Sep. 28, 2009, now U.S. Pat. No. 8,112,871, the entire contents of each of which being incorporated herein by reference.

BACKGROUND

Technical Field

The present disclosure relates to a method and system for manufacturing electrosurgical seal plates and, more particularly, to a method and system that employs photolithographic processes and systems operatively associated therewith to manufacture seal plates.

Background of Related Art

Electrosurgical forceps, e.g., bipolar or monopolar forceps, are commonly known in the medical art. Typically, the electrosurgical forceps are configured to, amongst other things, grasp and subsequently seal tissue. With this purpose in mind, the electrosurgical forceps, typically, include a pair of movable jaw members each having a respective seal plate operatively disposed thereon.

Typically, the seal plates disposed on the jaw members are configured to transfer electrosurgical energy having one or more frequencies to tissue to electrosurgically treat the tissue (e.g., seal tissue) and, in conjunction with a cutting element (e.g., knife blade), subsequently sever the sealed tissue. In certain instances, the seal plates may be configured to maintain a certain gap distance between the seal plates when the jaw members are in a closed position and tissue is grasped therebetween. As can be appreciated by one skilled in the art, the seal plates may be configured to perform and/or provide additional functions not described herein.

To provide the seal plates with the capability to seal, subsequently sever, and/or maintain a desired gap distance, the seal plates frequently are designed to include one or more features operatively disposed thereon or formed therewith. For example, in the instance where the seal plates are configured to subsequently sever tissue, one or both of the seal plates may include a knife slot configured to receive a knife blade. In the instance where the seal plates are configured to maintain a desired gap distance, one or both of the seal plates may include one or more stop members. In either instance, forming the seal plates during the manufacture process requires extremely high precession, which may lead to high tolerance stack-ups (e.g., knife blade to knife slot width ratios). Additionally, conventional means for positioning a stop member on a seal plate include bonding the stop member to a seal surface of the seal plate. In this instance, however, the bond and/or stop member that secures the stop member to the seal surface of the seal plate is susceptible to shear stresses associated with opening and closing the jaw members of an end effector assembly.

Conventional manufacture processes for seal plates may include stamping, punching, blanking, embossing, bending, flanging, coining, etc. In some instances, however, these manufacturing process may not be suitable for unique and/or complex jaw member and/or seal plate geometries, such as, for example, when one or both of the seal plates requires a knife slot or stop member formed thereon. Additionally, manufacture of the seal plates via the aforementioned process, in certain instances, may not be cost effective.

SUMMARY

The present disclosure provides a method of manufacture for an end effector assembly configured for use with an electrosurgical instrument configured for performing an electrosurgical procedure. The method includes providing a pair of jaw members. A step of the method includes forming one or more seal plates positionable on one of the pair of jaw members. Etching a dam along a side of the one or more seal plates is a step of the method, wherein the etched dam inhibits the flow of a plastic on the one or more seal plate such that a height of the plastic with respect to the at least one seal plate during an overmolding process may be controlled. The method includes positioning the one or more seal plates on the one of the pair of jaw members; and overmolding the seal plate to one or more of the pair of jaw members.

The present disclosure provides a method of manufacture for an end effector assembly configured for use with an electrosurgical instrument configured for performing an electrosurgical procedure. The method includes providing a pair of jaw members. A step of the method includes forming one or more seal plates positionable on one or more of a pair of jaw members associated with the end effector assembly. Etching a dam along a side of the one or more seal plates is a step of the method, wherein the etched dam inhibits the flow of a plastic on the one or more seal plates such that a height of the plastic with respect to the one or more seal plates during an overmolding process may be controlled. Etching a targeted retention feature along the side of the one or more seal plates is another step of the method. Etching one or more pockets on a seal surface of the one or more seal plates is yet another step of the method. The method includes depositing an adhesive into the one or more pockets on the one or more seal plates. A step of the method includes transferring a spacer from a location remote from the one or more pockets on the one or more seal plates to the one or more pockets on the at least one seal plate. Curing the adhesive and positioning the one or more seal plates on one of the pair of jaw members are steps of the method. Overmolding the seal plate to jaw member is still another step of the method.

The present disclosure also provides a system for the manufacture of an end effector assembly configured for use with an electrosurgical instrument configured for performing an electrosurgical procedure. The system includes a photolithography module configured to etch one or more pockets on a seal surface of the seal plate. The system includes a vacuum module configured to raise, transfer and lower a spacer from a location remote from the one or more pockets on the seal plate to the one or more pockets on the seal plate. The system includes an adhesive dispensing module configured to dispense an adhesive into the one or more pockets on the seal plate and allowing the adhesive to cure. The system may include an optical module configured to monitor a volume of adhesive dispensed within the one or more pockets and monitor placement of the spacer within the one or more pockets.

In an embodiment, the adhesive dispensing module includes a module to heat cure the adhesive after the spacer has been positioned within the at least one pocket.

In an embodiment, a retention feature is etched on the at least one seal plate and is configured to secure the at least one seal plate to at least one of a pair of jaw members of the end effector assembly.

In an embodiment, a knife slot is etched on the at least one seal plate and is configured to receive a knife blade of the electrosurgical instrument.

In an embodiment, one or both of the seal plate includes two or more materials laminated together, wherein the two or more materials is electrically conductive. In one particular embodiment, the two or more materials is selected from the group consisting of stainless steel, copper and ceramic. The copper may include etched heat sinks formed at predetermined locations on the at least one seal plate.

In an embodiment, the one or more seal plate includes a polyimide flex circuit, wherein the polyimide flex circuit is configured to provide electrical communication between the at least one seal plate and a source of electrosurgical energy. In one particular embodiment, the polyimide flex circuit includes a dialectic material having one or more etched through holes configured to create an electrical interconnection between the at least seal plate and the source of electrosurgical energy.

In an embodiment, one or both of the seal plates includes a textured surface, logo, and/or ruler etched thereon.

BRIEF DESCRIPTION OF THE DRAWINGS

Various embodiments of the present disclosure are described hereinbelow with references to the drawings, wherein.

DETAILED DESCRIPTION

Figure 1:
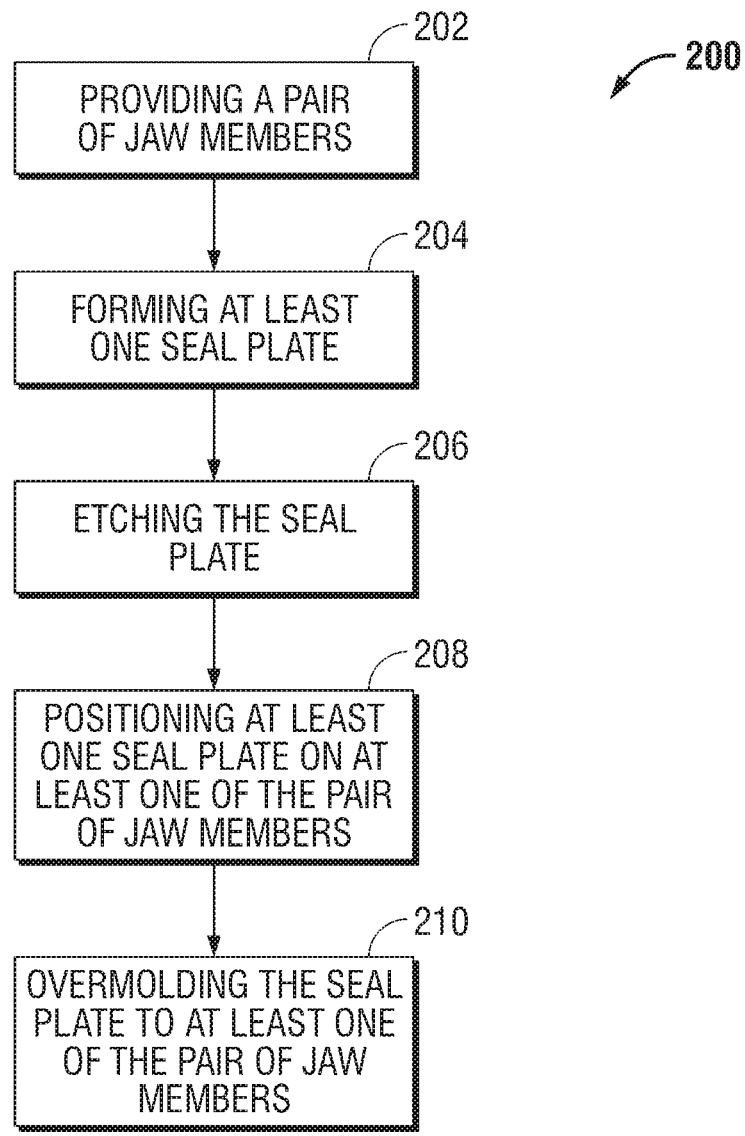
FIG. 1 is a flowchart illustrating steps for manufacturing a seal plate in accordance with an embodiment of the present disclosure.

Embodiments of the presently disclosed method and system are described in detail with reference to the drawing figures wherein like reference numerals identify similar or identical elements. As used herein, the term "distal" refers to that portion which is further from the user while the term "proximal" refers to that portion which is closer to the user.

The method and system of the present disclosure implements photolithographic processes in combination with etching processes to create specific, unique, complex geometries and/or features for seal plates used in the design of electrosurgical instruments, such as, for example, bipolar and monopolar electrosurgical devices. For example, possible features may include knife blade slots, recessed features, fine delicate features, and half etched features; all of which to be discussed in greater detail below. In addition to creating the aforementioned features, the precision of etching allows for greatly reduced tolerance stack-ups which could reduce issues with, for example, knife blade to knife slot ratios. Moreover, because the seal plates of the present disclosure are formed via suitable photolithographic and etching processes, the seal plates may be processed in lead frames that may be used in automated processes, which reduces costs associated with the aforementioned conventional manufacturing processes (e.g., stamping). Further, etch recipes associated with a given etch process, allow a user to enter practical data relating to the seal plate that may facilitate forming the seal plate during the etch process. For example, etch recipes associated with a given etch process may be tuned to have both vertical and non-vertical profiles, such as, when forming a knife slot on the seal plate.

With reference to FIG. 1, a flowchart illustrating a method of manufacture for an end effector assembly that includes a pair of jaw members each including a seal plate disposed thereon and configured for use with an electrosurgical instrument, e.g., electrosurgical forceps, in accordance with an embodiment of the present disclosure is shown designated 200.

An initial step of the method 200 includes providing a pair of jaw members (step 202) associated with an end effector adapted to connect to an electrosurgical forceps, such as, for example, a bipolar forceps. The jaw members may be formed by any suitable means, e.g., molding, casting, stamping, etc.

So as not to obscure the following disclosure with redundant information, manufacture of the seal plate is described herein as a single seal plate formed from a single sheet of material. Those skilled in the art will appreciate that a plurality of seal plates may be manufactured from a single sheet of material.

Figure 2:
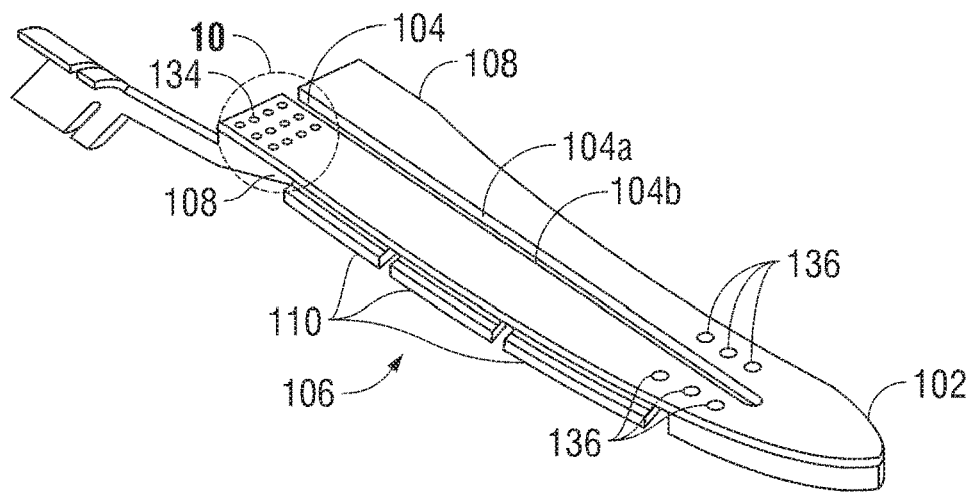
FIG. 2 is a side, perspective view of a seal plate according to an embodiment of the present disclosure and formed via the method of FIG. 1.
Figure 3A:
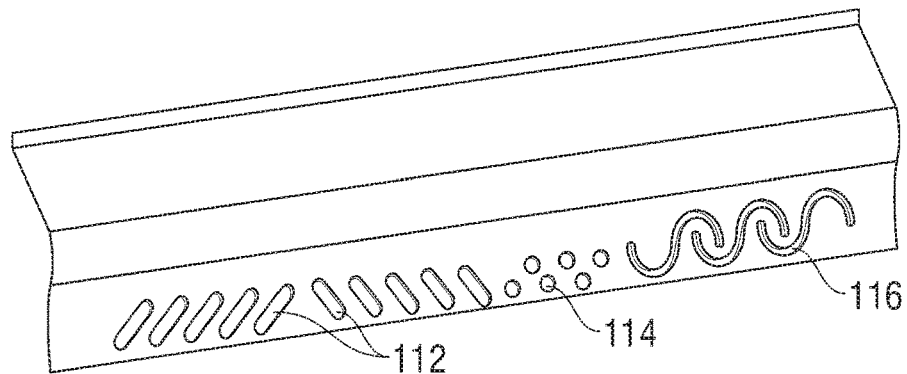
FIGS. 3A and 3B are perspective views of a seal plate according to an alternate embodiment of the present disclosure and formed via the method of FIG. 1.
Figure 3B:
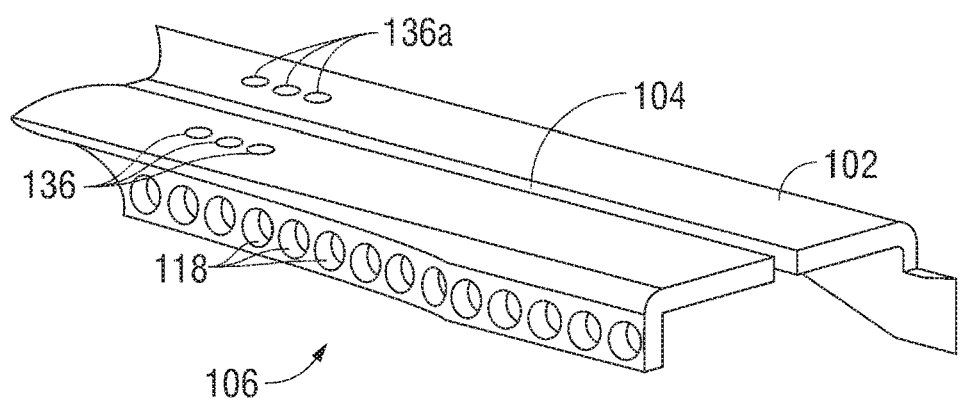

A step of method 200 includes forming a seal plate 102 (see step 204, in FIG. 1). Seal plate 102 may be formed from any suitable material, such as, for example, from a sheet of metal. A seal plate 102 formed according to method 200 is shown in FIG. 2. During formation of seal plate 102, seal plate 102 may be fully or partially etched (see step 206, in FIG. 1). For example, seal plate 102 may be etched to include one or more types of retention features 106. In the embodiment illustrated in FIG. 2, retention features 106 include a plurality etched flanges 110 that extend along one of a pair of sides 108 of the seal plate 102. In embodiments, retention features 106 may be partially etched in and/or fully etched through the seal plate 102. An example of partially etched retention features 106 is illustrated in FIG. 3A. More particularly, the partially etched retention features may be partially etched slots 112, partially etched cavities 114, and/or partially etched curved channels 116. An example of fully etched retention features 106 is illustrated in FIG. 3B. More particularly, the fully etched retention features 106 may be fully etched apertures 118. In either of the embodiments illustrated in FIGS. 2-3B, retention features 106 may be configured to securely retain the seal plate 102 to a respective jaw member of an end effector assembly associated with an electrosurgical forceps.

Figure 4:
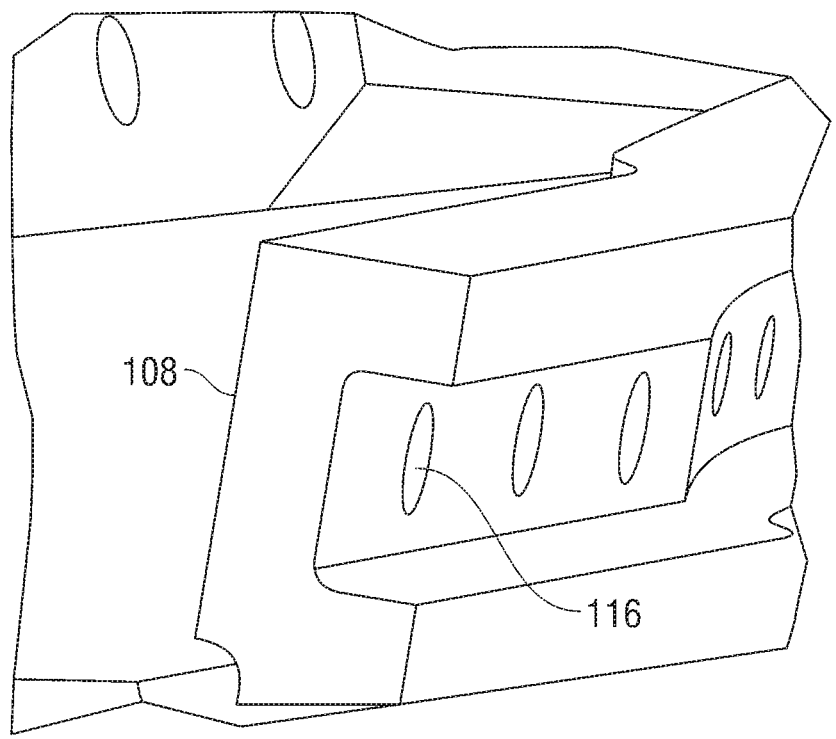
FIG. 4 is a perspective view of a seal plate according to an alternate embodiment of the present disclosure and formed via the method of FIG. 1.

A step of method 200 includes positioning the seal plate 102 on a respective jaw member and subsequently overmolding the seal plate 102 to a respective jaw member (see steps 208 and 210 respectively in FIG. 1). In an embodiment, the photolithographic and etch processes in accordance with the method 200 of the present disclosure may be implemented to create partial etch dams along a side 108 of the seal plate 102. More particularly, one or more partial etch dams 116 may be disposed and/or formed along one of the sides 108 of seal plate 102, see FIG. 4. Partial etch dam 116 is configured to control the height of an overmold during the overmolding process of the seal plate 102 to a respective jaw member of the end effector assembly. More particularly, the partial dam 116 is configured to inhibit the flow of a plastic during the overmolding process ensuring that the height of the plastic does not exceed a predetermined height on the seal plate 102 and/or the respective jaw member. Controlling and/or preventing the height of the plastic from exceeding a predetermined height on the seal plate 102 and/or a respective jaw member, e.g., jaw member 110 or 120, during the overmolding process, minimizes or "tightens" distribution of thermal spread during an electrosurgical procedure, e.g., electrosurgical sealing procedure. More particularly, the partial etch dam 116 creates a seal plate 102 having a consistent height across a length of the seal plate 102, which, in turn, provides a consistent seal across tissue and minimizes thermal spread to adjacent tissue. Experimentation on urethane coating processes confirms a relationship between seal plates having consistent (or inconsistent) seal plate heights and thermal spread. More particularly, thermal spread as a result of seal plates having consistent heights across a length of the seal plate was negligible when compared to seal plates having inconsistent heights across a length of the seal plate.

Figure 10:
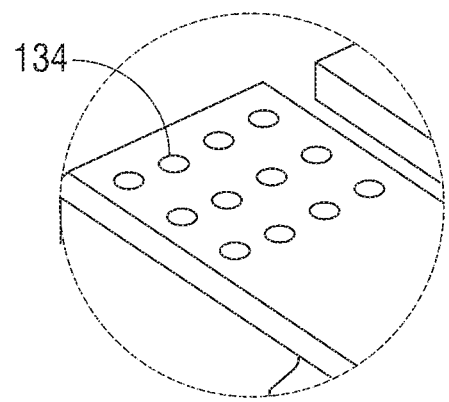
FIG. 10 is an area of detail of the seal plate illustrated in FIG. 1.

In an embodiment, the photolithographic and etching processes in accordance with the method 200 of the present disclosure may be employed to create one or more textured patterns on the seal plate 102. More particularly, one type of textured pattern may include, for example, a textured pattern 134 having a plurality of raised dots with varying dimensions etched on a portion of a seal surface 102a of the seal plate 102, see FIGS. 2 and 10.

Figure 5A:
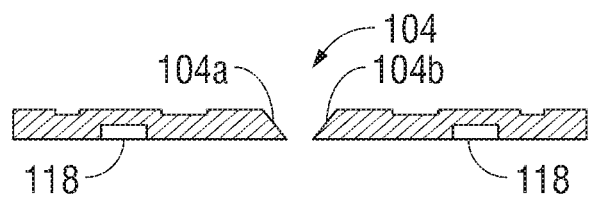
FIGS. 5A and 5B are respective cross-sectional views of a seal plate shown in a pre-formed and formed condition according to an alternate embodiment of the present disclosure and formed via the method of FIG. 1.
Figure 5B:
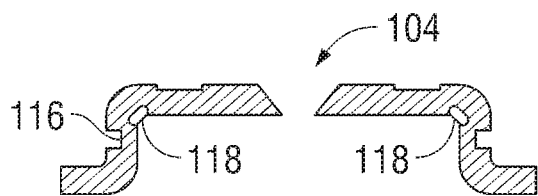
Figure 6:
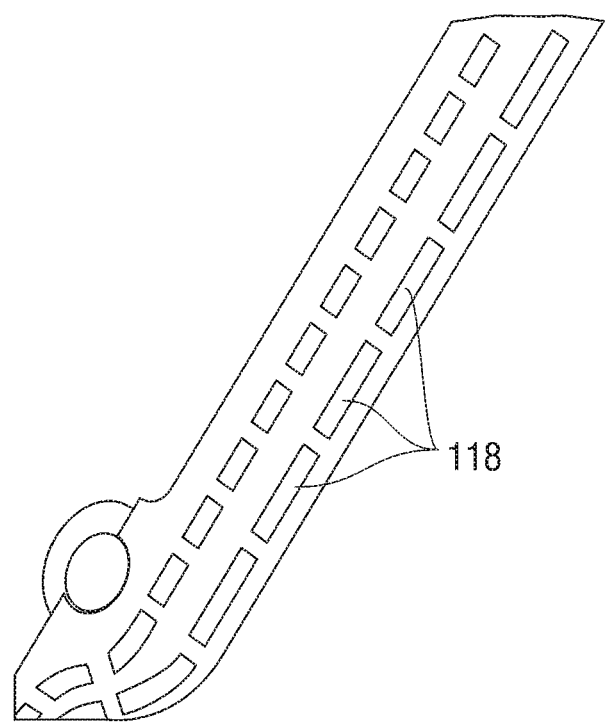
FIG. 6 is a perspective view of the seal plate of FIGS. 5A and 5B.
Figure 7:
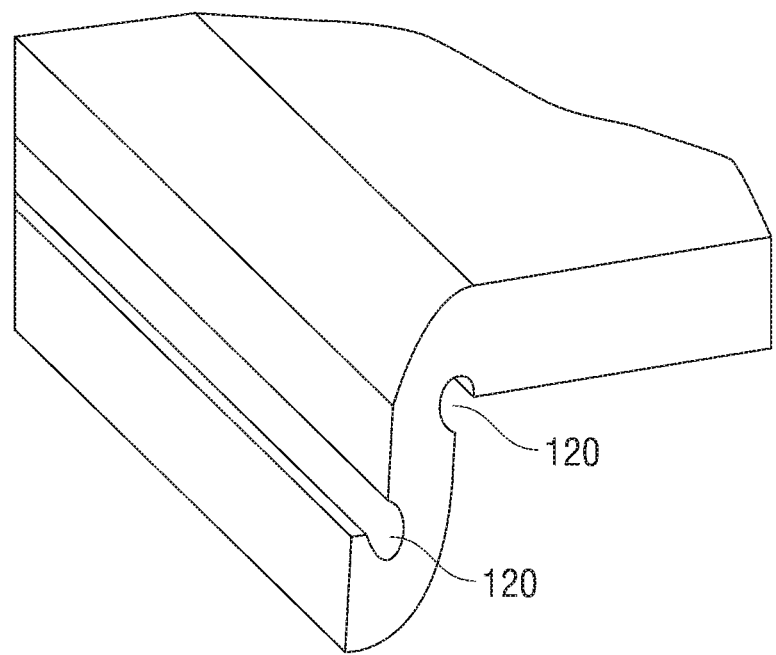
FIG. 7 is a perspective view of a seal plate according to an alternate embodiment of the present disclosure and formed via the method of FIG. 1.

With reference to FIGS. 5A and 5B, seal plate 102 is illustrated pre-formed and formed, respectively. In an embodiment, the photolithographic and etching processes in accordance with the method 200 of the present disclosure may be implemented to facilitate forming of the seal plate 102. More particularly, selectively and/or partially etching the seal plate 102 lightens the overall structure of the seal plate 102, which, in turn, facilitates bending of the seal plate 102 during the forming process. To this end, one or more areas of the seal plate 102 may be selectively and/or partially etched. More particularly, selectively and/or partially etched areas 118 of the seal plate 102 may be located at predetermined locations on the seal plate 102, see FIGS. 5A and 6. Additionally, partial etching may be implemented to create curves 120 with small, tight radii, see FIGS. 5B and 7, which also makes forming seal plate 102 easier.

With reference again to FIG. 2, in an embodiment, the photolithographic and etching processes in accordance with the method 200 of the present disclosure may be implemented to create a knife slot 104 on the seal plate 102. More particularly, a knife slot 104 may be fully etched through the seal plate 102. The high precision that is associated with known photolithographic and etching processes, allows a manufacturer to form a fully etched knife slot 104 with various geometries. More particularly, in embodiments, the fully etched knife slot 104 may be defined by a pair of inner facing walls 104a and 104b. Inner facing walls 104a and 104b may be etched to have any suitable configuration. The precise configuration of the inner facing walls 104a and 104b may be determined by a manufacturer and subsequently entered into an etch recipe for a given etch process. In the embodiment illustrated in FIG. 2, inner facing walls 104a and 104b are illustrated perpendicular with respect to the seal surface 102b of the seal plate 102. In the embodiment illustrated in FIGS. 5A and 5B, inner facing walls 104a and 104b are illustrated slanted or angled with respect to the seal surface 102b of the seal plate 102.

Figure 8:
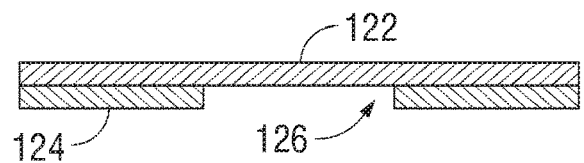
FIG. 8 is a cross-sectional view of a laminated seal plate according to an alternate embodiment of the present disclosure and formed via the method of FIG. 1.
Figure 9A:
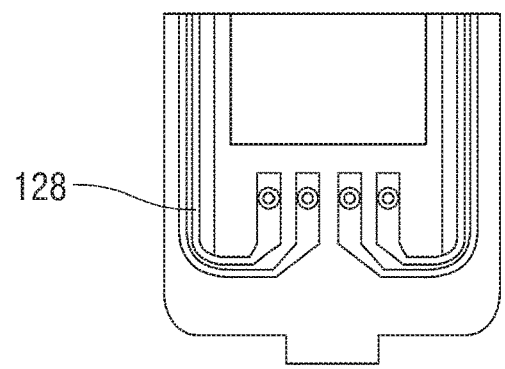
FIGS. 9A-9C is a seal plate including one or more points of electrical contact according to an alternate embodiment of the present disclosure and formed via the method of FIG. 1.
Figure 9B:
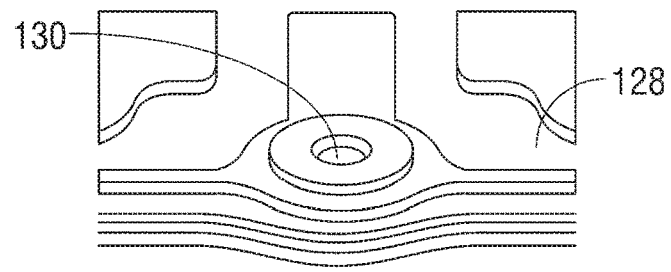
Figure 9C:
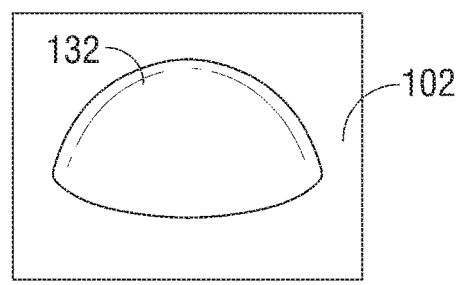

With reference to FIGS. 8-9B, in an embodiment, the photolithographic and etching processes in accordance with the method 200 of the present disclosure may be implemented to create selectively and/or partially etched areas on the seal plate 102 that are configured to provide one or more electrical points of contact on the seal plate 102 such that electrosurgical energy may be provided to the seal plate 102 and/or other electrical components associated therewith. More particularly, one or more materials may be laminated together and, subsequently, selectively and/or partially etched. The materials laminated together may be conductive, partially-conductive, or non-conductive. Suitable materials may include but are not limited to stainless steel, copper, silver, and the like.

In the embodiment illustrated in FIG. 8, a portion of the seal plate 102 includes layers of stainless steel 122 and copper 124 laminated together. In this embodiment, the layer of copper 124 is selectively etched. Etching the copper 124 in this manner may be used to create one or more etched areas 126 configured to receive one or more types of electrical interfaces. More particularly, an etched area 126 may be configured to receive integrated flex, e.g., a polyimide flex circuit 128 that is configured to provide electrosurgical energy to the seal plate 102, see FIG. 9A. In this instance, one or more through holes 130 may be fully etched to create electrical interconnections through dialectic material located on the polyimide flex (FIG. 9B). Additionally, seal plate 102 may include one or more partially or fully etched areas configured to receive a bead of solder 132 to create one or more electrical interconnections on the seal plate 102 which may result in electrical wiring being an integral component of the seal plate 102. In addition to the foregoing, laminating layers of material together and, subsequently, etching (e.g., partially or fully) one of the layers of material may be used to create heat sinks (not explicitly shown) at specific locations on the seal plate 102.

Figure 11A:
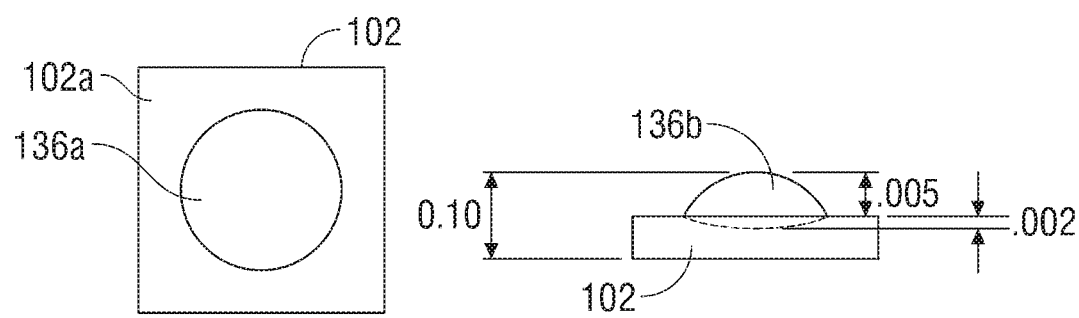
FIGS. 11A-11F are various configurations of spacers adapted for use with a seal plate formed via the method of FIG. 1.

As noted above, in certain instances the seal plates are configured to maintain a desired gap distance. With reference to FIGS. 11A-11F, in an embodiment, the photolithographic and etching processes in accordance with the method 200 of the present disclosure may be implemented to create one or more different types of insulation barriers, e.g., stop members, between seal plates associated with an end effector assembly. More particularly, photolithographic and etching processes of the present disclosure may be implemented to create one or more partially or fully etched recesses or pockets 136a on seal surface 102a of the seal plate 102 (see FIG. 11A, for example), wherein the pockets 136a is configured to receive one or more types of corresponding spacers 136b (FIG. 11A). An etched recess 136a may include an etch depth of 0.002 inches. Spacer 136b may be any suitable type of spacer known in the art. Spacer 136 may extend from seal surface 102a a distance that ranges from about 0.005 inches to about 0.01 inches. In an embodiment, spacer 136b may be a ceramic spacer made from aluminum titanium carbide, commonly referred to in the art and hereinafter referred to as AlTiC).

Figure 11B:
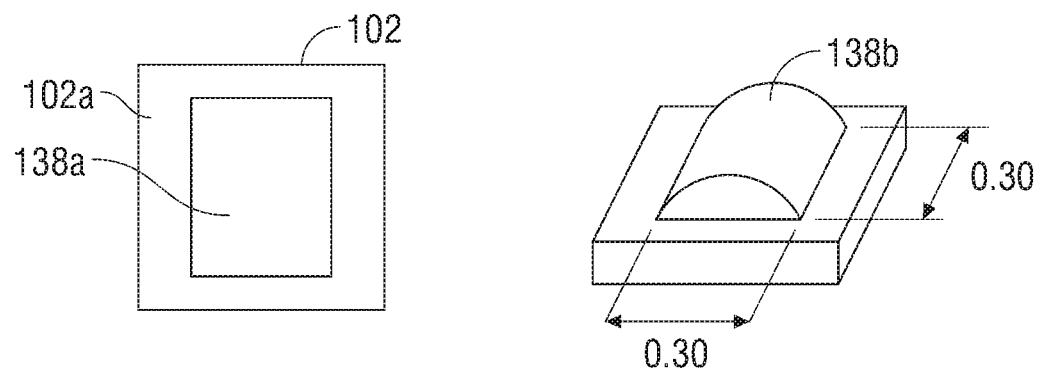
Figure 11C:
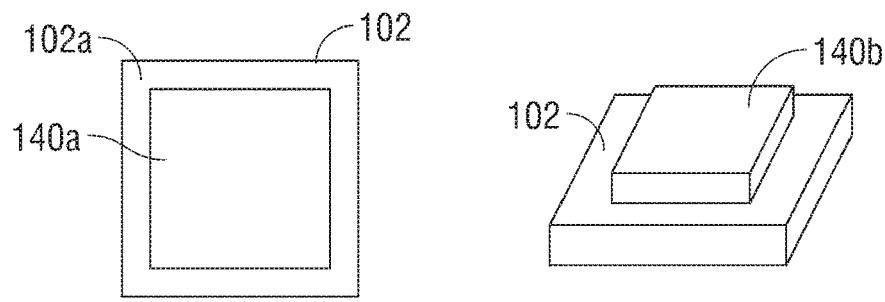
Figure 11D:
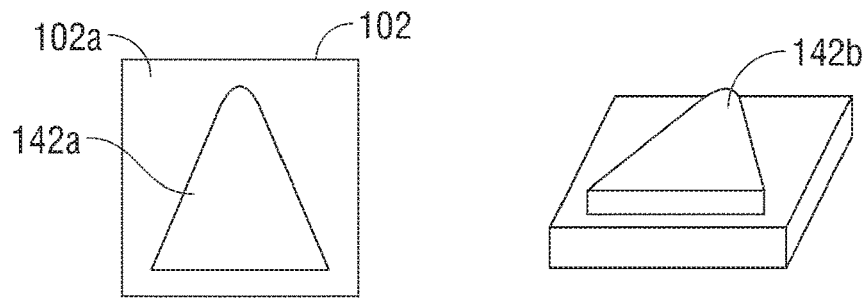
Figure 11E:
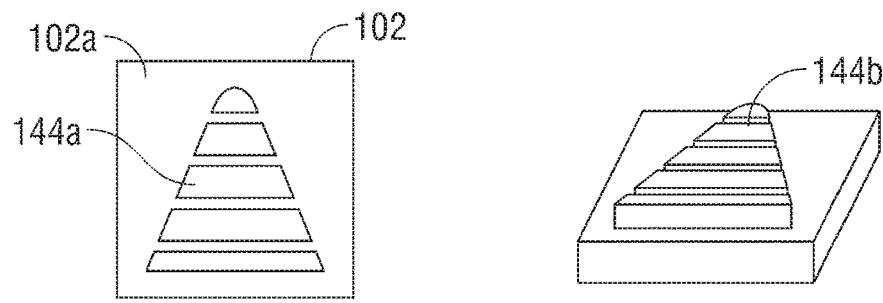
Figure 11F:
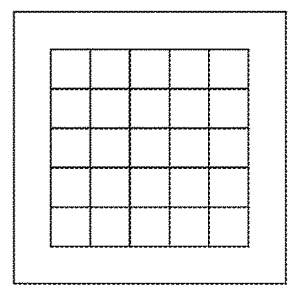

Etched recesses 136a and corresponding spacers 136b may have any suitable geometric configuration and may be dimension to fit within a 0.030×0.030 inch area (FIG. 11B). For example, FIG. 11A illustrates an etched recess 136a and corresponding spacer 136b each including a hemispherical configuration. FIG. 11B illustrates an etched recess 138a and corresponding spacer 138b each including a cylindrical configuration. FIG. 11C illustrates an etched recess 140a and corresponding spacer 140b each including a square configuration. FIG. 11D illustrates an etched recess 142a and corresponding spacer 142b each including a triangular configuration. FIG. 11E illustrates a plurality of etched recesses 144a and corresponding spacers 144b in an intermittent or staggered configuration. In embodiments, any of the aforementioned etched recesses and corresponding spacers may be arranged in a grid like configuration, see FIG. 11F for example. The combination of any of the aforementioned etched recesses, e.g., recess 138a and spacers, e.g., spacer 138b provides a user with the ability to manipulate how the jaw members 110 and 120 come together. For example, cylindrical shaped recess 138a and corresponding spacer 138b may be configured to force one of the jaw members, e.g., a upper jaw member 110 to roll along an axis of the spacer 138b when the upper jaw member 110 and a bottom jaw member 120 of an end effector assembly are moved toward each other, which, in turn, results in a more precise alignment of the upper and lower jaw members 110 and 120, respectively.

Moreover, the combination of any of the aforementioned etched recesses, e.g., recess 136a and spacers, e.g., spacer 136b increases the integrity of a bond between the seal surface 102a and spacer 136b in that the spacer 136b is encased within a recess 136b, as opposed to only being bonded to the seal surface 102a of the seal plate 102. The photolithographic and etching processes in accordance with the method 200 of the present disclosure allows a manufacturer to position any of the aforementioned spacers, e.g., spacer 136b within a corresponding pocket 136a to within a 0.0005 inch tolerance.

Figure 12:
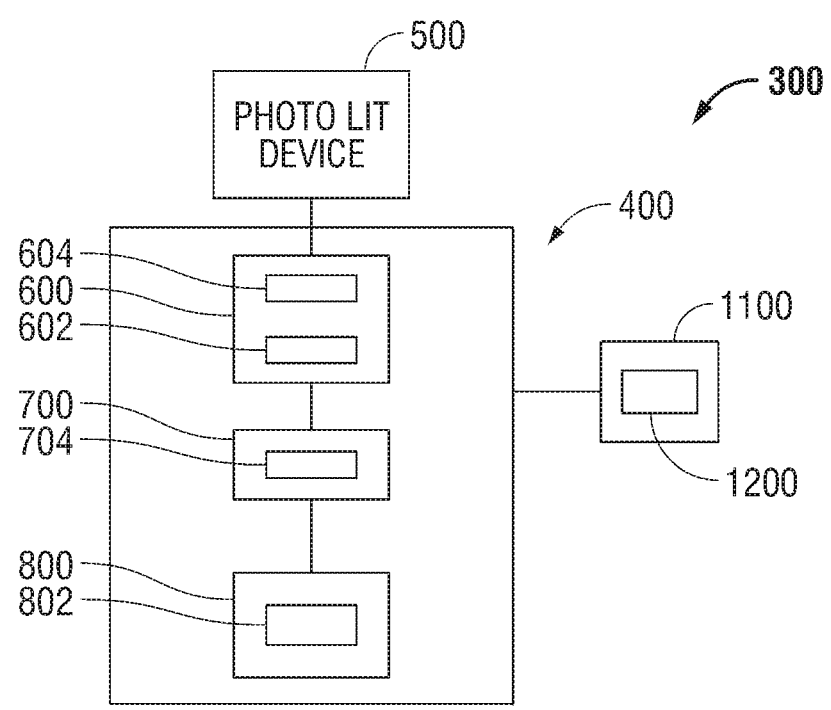
FIG. 12 illustrates a block diagram of a system adapted for use with the method of FIG. 1 and configured to position one of the various spacers depicted in FIGS. 11A-11F within a seal plate formed via the method of FIG. 1.
Figure 13A:
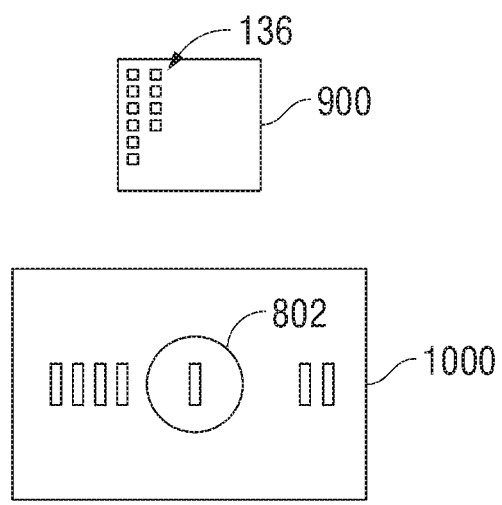
FIGS. 13A and 13B are functional block diagrams of a method of use of the system of FIG. 12.
Figure 13B:
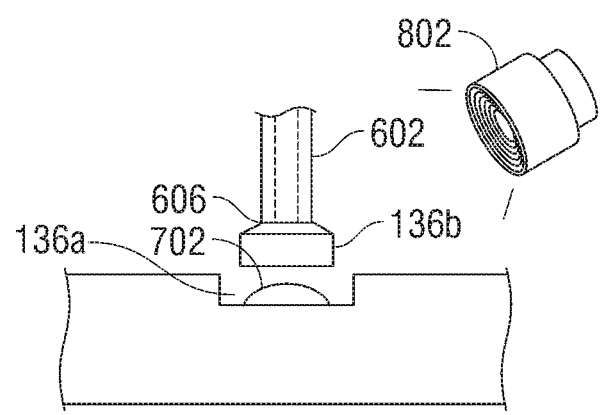

With reference now to FIGS. 12-13B, in an embodiment, a step of the method 200 may include etching one or more recesses, e.g., 136a on the seal surface 102a of the seal plate 102 and positioning a spacer, e.g., spacer 136b in the recess 136a. In this instance, an automated system 300 is provided and includes a plurality of modules 400 that includes a vacuum module 600, an adhesive dispensing module 700, and an optional optical module 800. Each of the foregoing modules is fully automated and in operative communication with a photolithography module 500 (configured to provide functions previously described herein) that is also fully automated.

Photolithography module 500 is configured to fully, partially, and/or selectively etch one or more pockets 136b on the seal surface 102a of the seal plate 102. After the pockets 136b have been etched into the seal surface 102a of the seal plate 102, the seal plate 102 is transferred to adhesive dispensing module 700 where a bead of adhesive 702 will be dispensed into the pocket 136b such that a spacer 136a may be positioned into the pocket 136b and bonded therein.

Vacuum module 600 is configured to raise and transfer a spacer, e.g., spacer 136b from a loading module 900 (a loading table 900, for example) to the one or more pockets 136a on the seal plate 102 and lower the spacer 136b within the pocket 136a on the seal plate 102. With this purpose mind, the vacuum module 600 includes one or more vacuum transfer devices 602 operatively connected to a vacuum source 604. Vacuum transfer device 602 may be any suitable device that is capable of raising, transferring and lowering a spacer 136b. For example, vacuum devices typically associated with the manufacture process of disk drives, auto slider bond, SMT automated assembly and PCB assembly may be utilized in combination with vacuum module 600. In an embodiment, the vacuum transfer device 602 (e.g., vacuum device typically utilized in the manufacture process PCB assembly) includes a distal end 606 configured to raise a spacer 136b (FIG. 13) from loading table 900, transfer the spacer 136b to the recess 136a, and, subsequently, lower the spacer 136b within the recess 136a.

Adhesive dispensing module 700 is configured to dispense a bead of suitable adhesive 702 into the one or more pockets 136a on the seal plate 102. In an embodiment, the adhesive dispensing module includes a device 704 configured to heat cure the adhesive 702 after the spacer 136b has been positioned within the pocket 136a.

In an embodiment, an optical module 800 is provided and is configured to monitor the volume of adhesive 702 dispensed within the pocket 136a, monitor alignment of the spacer 136b with respect to pocket 136a and/or monitor placement of the spacer 136b within the pocket 136a. To this end, optical module 800 may include one or more types of camera 802 located at or near the adhesive dispensing module 700.

System 300 includes one or more microprocessors 1100 including one or more algorithms 1200 configured to control and monitor each of the above-referenced modules during transferring and positioning of the spacers 136b within the pockets 136a. System 300 employs an x-y coordinate axis system to facilitate properly aligning a spacer 136b and pocket 136a (FIG. 13A).

In use, the vacuum transfer device 602 of vacuum module 600 is used to raise one of a plurality of spacers 136b from a loading table 900 to an adhesive station 1000 where the seal plate 102 is located. At a time prior to the spacer 136b arriving at the adhesive station 1000, adhesive dispensing module 700 dispenses a bead of adhesive 702 (FIG. 13B) within a pocket 136a. The time the bead of adhesive 702 is dispensed will depend on such parameters as type of adhesive, cure time of adhesive, volume of adhesive, etc. Camera 802 of optical module 800 may be employed to ensure that the spacer 136b and pocket 136a are properly aligned. Once it is determined that the spacer 136a and pocket 136b are properly aligned, the vacuum transfer device 602 may be employed to lower the spacer 136b into pocket 136a.

Camera 802 of optical module 800 may again be employed to ensure that the spacer 136b seats at a proper height above pocket 136a (FIG. 13B). In accordance with the present disclosure spacer 136b seats at a height above the pocket 136a that ranges from about 0.001 inches to about 0.006 inches. Once it is determined that the spacer 136b seats at a proper height above pocket 136a, ultra violet heat may be applied to facilitate the curing process.

From the foregoing and with reference to the various figure drawings, those skilled in the art will appreciate that certain modifications can also be made to the present disclosure without departing from the scope of the same.

While several embodiments of the disclosure have been shown in the drawings, it is not intended that the disclosure be limited thereto, as it is intended that the disclosure be as broad in scope as the art will allow and that the specification be read likewise. Therefore, the above description should not be construed as limiting, but merely as exemplifications of particular embodiments. Those skilled in the art will envision other modifications within the scope and spirit of the claims appended hereto.

What is claimed is:

1. An end effector configured for use with an electrosurgical device, the end effector comprising:
   a first jaw member including a seal plate, the seal plate including a plurality of retention features configured to operably engage the seal plate to an overmolding material; and
   a second jaw member operably coupled to the first jaw member such that at least one of the first jaw member or the second jaw member is movable relative to the other between an open condition and a closed condition, the second jaw member including a seal surface including a recess defined therein.

2. The end effector according to claim 1, wherein the first jaw member is movable relative to the second jaw member.

3. The end effector according to claim 1, wherein the second jaw member is movable relative to the first jaw member.

4. The end effector according to claim 1, further comprising a spacer extending from the recess and configured to maintain a gap distance between the seal plate of the first jaw member and the seal surface of the second jaw member when the first and second jaw members are in the closed condition.

5. The end effector according to claim 4, wherein the spacer extends above the seal surface of the second jaw member a distance in a range from about 0.001 inches to about 0.006 inches.

6. The end effector according to claim 4, wherein the spacer includes a hemispherical configuration.

7. The end effector according to claim 4, wherein the spacer includes a cylindrical configuration.

8. The end effector according to claim 4, wherein the spacer includes a square configuration.

9. The end effector according to claim 4, wherein the spacer includes a triangular configuration.

10. The end effector according to claim 4, further comprising an adhesive disposed within the recess and configured to retain the spacer within the recess.

11. The end effector according to claim 1, wherein a plurality of spacers is disposed within the recess.

12. The end effector according to claim 11, wherein the plurality of spacers is arranged in a grid-like configuration.

13. The end effector according to claim 1, wherein at least one of the seal plate of the first jaw member or the seal surface of the second jaw member includes a knife slot defined therein.

14. The end effector according to claim 1, wherein the seal surface of the second jaw member includes a knife slot defined therein and a first spacer is disposed within the recess on a first side of the knife slot and a second spacer is disposed in a second recess defined within the seal surface on a second side of the knife slot.

15. The end effector according to claim 1, wherein each retention feature of the plurality of retention features extends from a side of the seal plate.

16. The end effector according to claim 1, wherein the plurality of retention features defines a curved portion configured to secure the seal plate to the overmolding material.

17. The end effector according to claim 1, wherein the recess is configured to accommodate a spacer.

18. The end effector according to claim 1, further comprising a spacer operably coupled to at least one of the first jaw member or the second jaw member and configured to maintain a gap distance between the first seal plate of the first jaw member and the seal surface of the second jaw member when the first and second jaw members are in the closed condition.

* * * * *